(12) United States Patent
Park et al.

(10) Patent No.: US 12,730,475 B2
(45) Date of Patent: Sep. 8, 2026

(54) WEARABLE ELECTRONIC DEVICE AND METHOD OF OPERATING THE SAME

(71) Applicant: Samsung Electronics Co., Ltd., Suwon-si (KR)

(72) Inventors: Hyuncheol Park, Suwon-si (KR); Hyoujoo Kwon, Suwon-si (KR); Jeongmin Park, Suwon-si (KR); Hongji Lee, Suwon-si (KR); Sunok Jung, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 679 days.

(21) Appl. No.: 18/168,778

(22) Filed: Feb. 14, 2023

(65) Prior Publication Data

US 2023/0185335 A1 Jun. 15, 2023

Related U.S. Application Data

(63) Continuation of application No. PCT/KR2022/012517, filed on Aug. 22, 2022.

(30) Foreign Application Priority Data

Oct. 27, 2021 (KR) ........................ 10-2021-0144292
Mar. 30, 2022 (KR) ........................ 10-2022-0039629

(51) Int. Cl.
*G06F 1/16* (2006.01)
*A61B 5/00* (2006.01)
*G06F 3/01* (2006.01)

(52) U.S. Cl.
CPC ............. *G06F 1/163* (2013.01); *A61B 5/681* (2013.01); *G06F 3/011* (2013.01)

(58) Field of Classification Search
CPC ... A61B 5/01; A61B 5/681; A61B 2562/0271; A61B 5/6803; A61B 5/02438; G06F 3/011; G06F 1/206; G01K 13/20
See application file for complete search history.

(56) References Cited

U.S. PATENT DOCUMENTS 10,563,878 B2 2/2020 Tang
11,426,079 B1 * 8/2022 Sunden .................. G16H 50/30
(Continued)

FOREIGN PATENT DOCUMENTS

CN 108344526 B 7/2018
CN 111855020 A 10/2020
(Continued)

OTHER PUBLICATIONS

Extended European Search Report dated Oct. 2, 2024 for EP Application No. 22887313.9.
(Continued)

*Primary Examiner* — Gerald Johnson
(74) *Attorney, Agent, or Firm* — Nixon & Vanderhye P.C.

(57) ABSTRACT

A wearable electronic device is provided. The wearable electronic device includes at least one first thermistor arranged in different heat generation positions in the wearable electronic device and configured to detect a temperature change of internal elements of the wearable electronic device, a temperature sensor configured to calculate a body temperature of a user based on the temperature change of the internal elements and a skin temperature trend of the user, and at least one processor configured to determine whether an internal temperature by the internal elements in the wearable electronic device is within a reference temperature range that does not have an influence on a calculation of the body temperature, based on a measured value of the at least one first thermistor, determine a user state index (UI) indicating whether the user is in a state in which the body
(Continued)

temperature is measurable, when the internal temperature is determined to be within the reference temperature range, and measure the body temperature by adjusting a body temperature measurement period based on the UI.

20 Claims, 16 Drawing Sheets

(56) References Cited

U.S. PATENT DOCUMENTS

| | | | | |
|---|---|---|---|---|
| 2015/0374310 | A1 | 12/2015 | Lee | |
| 2016/0062326 | A1 | 3/2016 | Bang et al. | |
| 2016/0213325 | A1 | 7/2016 | Sogo et al. | |
| 2019/0021701 | A1 | 1/2019 | Vardi et al. | |
| 2021/0022676 | A1 * | 1/2021 | Lamego | A61B 5/369 |

FOREIGN PATENT DOCUMENTS

| | | | | | |
|---|---|---|---|---|---|
| CN | 114623948 | A | * | 6/2022 | A61B 5/681 |
| JP | 2007117270 | A | | 5/2007 | |
| JP | 2015-27431 | A | | 2/2015 | |
| JP | 5910309 | B2 | | 4/2016 | |
| JP | 2017-060009 | A | | 3/2017 | |
| JP | 2019-176932 | A | | 10/2019 | |
| JP | 6799413 | B2 | | 12/2020 | |
| KR | 10-2012-0010723 | A | | 2/2012 | |
| KR | 10-2013-0103038 | A | | 9/2013 | |
| KR | 10-2016-0006409 | A | | 1/2016 | |
| KR | 10-2016-0026329 | A | | 3/2016 | |
| KR | 10-1727070 | B1 | | 4/2017 | |
| KR | 10-2017-0133087 | A | | 12/2017 | |
| KR | 10-2021-0001844 | A | | 1/2021 | |

OTHER PUBLICATIONS

International Search Report dated Nov. 24, 2022, issued in an International Application No. PCT/KR2022/012517.

* cited by examiner

| | | |
|---|---|---|
| 1 | Scalp | 34.8 |
| 2 | Chest | 34.5 |
| 3 | Axilla | 36.4 |
| 4 | Arm | 33.5 |
| 5 | Finger | 33.2 |
| 6 | Thigh | 33.4 |
| 7 | Leg | 30.1 |
| 8 | Foot | 29.7 |
| 9 | Toe | 29.1 |

1130

| UI | Measurement period | State |
|---|---|---|
| 0 | MAX·(60m) | Stable |
| 1 | 30m | Normal |
| 2 | 10m | Unstable |
| 3 | MIN·(5m,·initial value) | Extremely unstable |

Display measured body temperature values

WEARABLE ELECTRONIC DEVICE AND METHOD OF OPERATING THE SAME

CROSS-REFERENCE TO RELATED APPLICATION(S)

This application is a continuation application, claiming priority under § 365(c), of an International application No. PCT/KR2022/012517, filed on Aug. 22, 2022, which is based on and claims the benefit of a Korean patent application number 10-2021-0144292, filed on Oct. 27, 2021, in the Korean Intellectual Property Office, and of a Korean patent application number 10-2022-0039629, filed on Mar. 30, 2022, in the Korean Intellectual Property Office, the disclosure of each of which is incorporated by reference herein in its entirety.

BACKGROUND

1. Field

The disclosure relates to a wearable electronic device. More particularly, the disclosure relates to a method of operating the wearable electronic device.

2. Description of Related Art

A wearable electronic device may refer to an electronic device that is used in close contact with a user's body beyond a portable device, for example, a smartphone or a notebook computer. The wearable electronic device may take the form of, for example, glasses, a watch, or a head-mounted display (HMD), and may be connected to a smartphone or may independently perform various functions. Unlike smartphones or notebook computers, which need to be taken out and checked all the time, users can more conveniently perform, for example, simple checking of text messages or e-mails, health management, such as checking of a heart rate and calculating of an exercise amount, an exercise function, and schedule management, using wearable electronic devices.

SUMMARY

A commercial thermometer does not support continuous measurement, and a device equipped with an infrared (IR) non-contact temperature sensor capable of ensuring an accuracy at a level of a medical device may not have a continuous measurement function. In addition, a device with a function of estimating a body temperature with a contact temperature sensor may support continuous measurement, but may have a relatively low accuracy and may require a large amount of time to measure a change in a body temperature. In addition, due to a constant measurement period, it is virtually impossible to check a heat condition of a user in real time.

Aspects of the disclosure are to address at least the above-mentioned problems and/or disadvantages and to provide at least the advantages described below. Accordingly, an aspect of the disclosure is to provide a method and apparatus for continuing to measure a body temperature of a user accurately and automatically.

Additional aspects will be set forth in part in the description which follows and, in part, will be apparent from the description, or may be learned by practice of the presented embodiments.

In accordance with an aspect of the disclosure, a wearable electronic device is provided. The wearable electronic device includes at least one first thermistor arranged in different heat generation positions in the wearable electronic device and configured to detect a temperature change of internal elements of the wearable electronic device, a temperature sensor configured to calculate a body temperature of a user based on the temperature change of the internal elements and a skin temperature trend of the user, and at least one processor configured to determine whether an internal temperature by the internal elements in the wearable electronic device is within a reference temperature range that does not have an influence on a calculation of the body temperature, based on a measured value of the at least one first thermistor, determine a user state index (UI) indicating whether the user is in a state in which the body temperature is measurable, when the internal temperature is determined to be within the reference temperature range, and measure the body temperature by adjusting a body temperature measurement period based on the UI.

In accordance with another aspect of the disclosure, a method of operating a wearable electronic device is provided. The method includes determining whether the wearable electronic device is worn, determining whether an internal temperature by internal elements of the wearable electronic device is within a reference temperature range that does not have an influence on a measurement of a body temperature of a user, based on whether the wearable electronic device is worn, determining a UI indicating whether the user is in a state in which the body temperature is measurable, when the internal temperature is determined to be within the reference temperature range, and measuring the body temperature by adjusting a body temperature measurement period based on the UI.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description, taken in conjunction with the accompanying drawings, in which.

Throughout the drawings, like reference numerals will be understood to refer to like parts, components, and structures.

DETAILED DESCRIPTION

Figure 1:
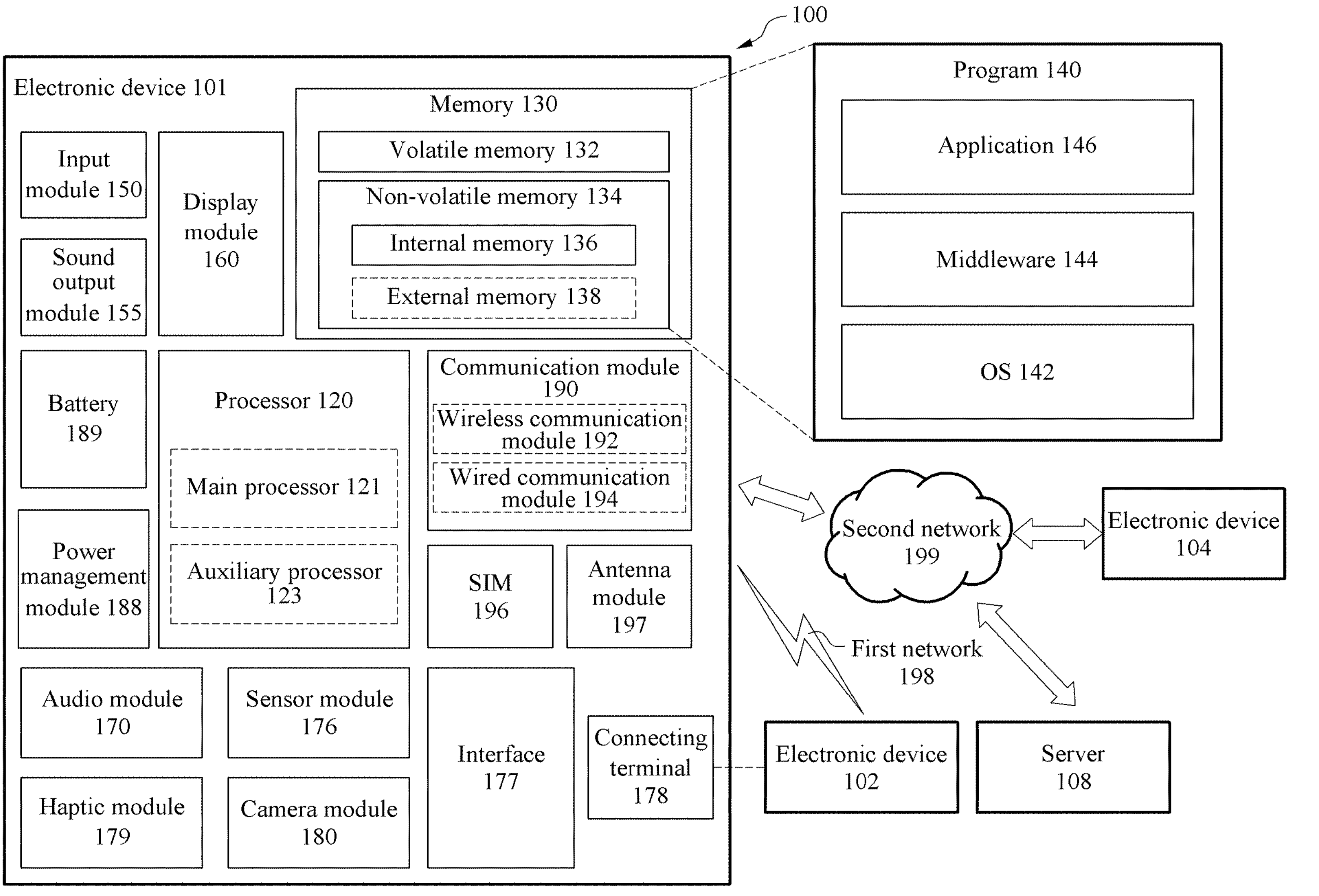
FIG. 1 is a block diagram illustrating an electronic device in a network environment according to an embodiment of the disclosure.

Hereinafter, embodiments will be described in detail with reference to the accompanying drawings. When describing the embodiments with reference to the accompanying drawings, like reference numerals refer to like elements and any repeated description related thereto will be omitted.

FIG. 1 is a block diagram illustrating an electronic device in a network environment according to an embodiment of the disclosure.

Referring to FIG. 1, an electronic device 101 in a network environment 100 may communicate with an electronic device 102 via a first network 198 (e.g., a short-range wireless communication network), or communicate with at least one of an electronic device 104 or a server 108 via a second network 199 (e.g., a long-range wireless communication network). According to an embodiment of the disclosure, the electronic device 101 may communicate with the electronic device 104 via the server 108. According to an embodiment of the disclosure, the electronic device 101 may include a processor 120, a memory 130, an input module 150, a sound output module 155, a display module 160, an audio module 170, and a sensor module 176, an interface 177, a connecting terminal 178, a haptic module 179, a camera module 180, a power management module 188, a battery 189, a communication module 190, a subscriber identification module (SIM) 196, or an antenna module 197. In some embodiment of the disclosure, at least one of the components (e.g., the connecting terminal 178) may be omitted from the electronic device 101, or one or more other components may be added in the electronic device 101. In some embodiments of the disclosure, some of the components (e.g., the sensor module 176, the camera module 180, or the antenna module 197) may be integrated as a single component (e.g., the display module 160).

The processor 120 may execute, for example, software (e.g., a program 140) to control at least one other component (e.g., a hardware or software component) of the electronic device 101 connected to the processor 120, and may perform various data processing or computation. According to an embodiment of the disclosure, as at least a part of data processing or computation, the processor 120 may store a command or data received from another component (e.g., the sensor module 176 or the communication module 190) in a volatile memory 132, process the command or the data stored in the volatile memory 132, and store resulting data in a non-volatile memory 134. According to an embodiment of the disclosure, the processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with the main processor 121. For example, when the electronic device 101 includes the main processor 121 and the auxiliary processor 123, the auxiliary processor 123 may be adapted to consume less power than the main processor 121 or to be specific to a specified function. The auxiliary processor 123 may be implemented separately from the main processor 121 or as a part of the main processor 121.

The auxiliary processor 123 may control at least some of functions or states related to at least one (e.g., the display module 160, the sensor module 176, or the communication module 190) of the components of the electronic device 101, instead of the main processor 121 while the main processor 121 is in an inactive (e.g., a sleep) state or along with the main processor 121 while the main processor 121 is an active state (e.g., executing an application). According to an embodiment of the disclosure, the auxiliary processor 123 (e.g., an ISP or a CP) may be implemented as a portion of another component (e.g., the camera module 180 or the communication module 190) that is functionally related to the auxiliary processor 123. According to an embodiment of the disclosure, the auxiliary processor 123 (e.g., an NPU) may include a hardware structure specified for artificial intelligence model processing. An artificial intelligence model may be generated by machine learning. Such learning may be performed by, for example, the electronic device 101 in which artificial intelligence is performed, or performed via a separate server (e.g., the server 108). Learning algorithms may include, but are not limited to, for example, supervised learning, unsupervised learning, semi-supervised learning, or reinforcement learning. The AI model may include a plurality of artificial neural network layers. An artificial neural network may include, for example, a deep neural network (DNN), a convolutional neural network (CNN), a recurrent neural network (RNN), a restricted Boltzmann machine (RBM), a deep belief network (DBN), and a bidirectional recurrent deep neural network (BRDNN), a deep Q-network, or a combination of two or more thereof, but is not limited thereto. The AI model may additionally or alternatively include a software structure other than the hardware structure.

The memory 130 may store various pieces of data used by at least one component (e.g., the processor 120 or the sensor module 176) of the electronic device 101. The various pieces of data may include, for example, software (e.g., the program 140) and input data or output data for a command related thereto. The memory 130 may include the volatile memory 132 or the non-volatile memory 134.

The program 140 may be stored as software in the memory 130, and may include, for example, an operating system (OS) 142, middleware 144, or an application 146.

The input module 150 may receive a command or data to be used by another component (e.g., the processor 120) of the electronic device 101, from the outside (e.g., a user) of the electronic device 101. The input module 150 may include, for example, a microphone, a mouse, a keyboard, a key (e.g., a button), or a digital pen (e.g., a stylus pen).

The sound output module 155 may output a sound signal to the outside of the electronic device 101. The sound output module 155 may include, for example, a speaker or a receiver. The speaker may be used for general purposes, such as playing multimedia or playing record. The receiver may be used to receive an incoming call. According to an embodiment of the disclosure, the receiver may be implemented separately from the speaker or as a part of the speaker.

The display module 160 may visually provide information to the outside (e.g., a user) of the electronic device 101. The display module 160 may include, for example, a control circuit for controlling a display, a hologram device, or a projector and control circuitry to control a corresponding one of the display, the hologram device, and the projector. According to an embodiment of the disclosure, the display module 160 may include a touch sensor adapted to detect a touch, or a pressure sensor adapted to measure the intensity of force incurred by the touch.

The audio module 170 may convert a sound into an electric signal or vice versa. According to an embodiment of the disclosure, the audio module 170 may obtain the sound via the input module 150 or output the sound via the sound output module 155 or an external electronic device (e.g., the electronic device 102, such as a speaker or a headphone) directly or wirelessly connected to the electronic device 101.

The sensor module 176 may detect an operational state (e.g., power or temperature) of the electronic device 101 or an environmental state (e.g., a state of a user) external to the electronic device 101, and generate an electric signal or data value corresponding to the detected state. According to an embodiment of the disclosure, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., by wire) or wirelessly. According to an embodiment of the disclosure, the interface 177 may include, for example, a high-definition multimedia interface (HDMI), a universal serial bus (USB) interface, a secure digital (SD) card interface, or an audio interface.

The connecting terminal 178 may include a connector via which the electronic device 101 may be physically connected to an external electronic device (e.g., the electronic device 102). According to an embodiment of the disclosure, the connecting terminal 178 may include, for example, an HDMI connector, a USB connector, an SD card connector, or an audio connector (e.g., a headphone connector).

The haptic module 179 may convert an electric signal into a mechanical stimulus (e.g., a vibration or a movement) or an electrical stimulus which may be recognized by a user via his or her tactile sensation or kinesthetic sensation. According to an embodiment of the disclosure, the haptic module 179 may include, for example, a motor, a piezoelectric element, or an electric stimulator.

The camera module 180 may capture a still image and moving images. According to an embodiment of the disclosure, the camera module 180 may include one or more lenses, image sensors, image signal processors, or flashes.

The power management module 188 may manage power supplied to the electronic device 101. According to an embodiment of the disclosure, the power management module 188 may be implemented as, for example, at least a part of a power management integrated circuit (PMIC).

The battery 189 may supply power to at least one component of the electronic device 101. According to an embodiment of the disclosure, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more CPs that are operable independently of the processor 120 (e.g., an AP) and that support a direct (e.g., wired) communication or a wireless communication. According to an embodiment of the disclosure, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module, or a power line communication (PLC) module). A corresponding one of these communication modules may communicate with the external electronic device 104 via the first network 198 (e.g., a short-range communication network, such as Bluetooth™, wireless-fidelity (Wi-Fi) direct, or infrared data association (IrDA)) or the second network 199 (e.g., a long-range communication network, such as a legacy cellular network, a 5th generation (5G) network, a next-generation communication network, the Internet, or a computer network (e.g., a LAN or a wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the SIM 196.

The wireless communication module 192 may support a 5G network after a 4th generation (4G) network, and a next-generation communication technology, e.g., a new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., a millimeter wave (mmWave) band) to achieve, e.g., a high data transmission rate. The wireless communication module 192 may support various technologies for securing performance on a high-frequency band, such as, e.g., beamforming, massive multiple-input and multiple-output (MIMO), full dimensional MIMO (FD-MIMO), an array antenna, analog beam-forming, or a large-scale antenna. The wireless communication module 192 may support various requirements specified in the electronic device 101, an external electronic device (e.g., the electronic device 104), or a network system (e.g., the second network 199). According to an embodiment of the disclosure, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device) of the electronic device 101. According to an embodiment of the disclosure, the antenna module 197 may include an antenna including a radiating element including a conductive material or a conductive pattern formed in or on a substrate (e.g., a printed circuit board (PCB)). According to an embodiment of the disclosure, the antenna module 197 may include a plurality of antennas (e.g., array antennas). In such a case, at least one antenna appropriate for a communication scheme used in a communication network, such as the first network 198 or the second network 199, may be selected by, for example, the communication module 190 from the plurality of antennas. The signal or the power may be transmitted or received between the communication module 190 and the external electronic device via the at least one selected antenna. According to an embodiment of the disclosure, another component (e.g., a radio frequency integrated circuit (RFIC)) other than the radiating element may be additionally formed as a part of the antenna module 197.

According to various embodiments of the disclosure, the antenna module 197 may form a mmWave antenna module. According to an embodiment of the disclosure, the mmWave antenna module may include a printed circuit board, an RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment of the disclosure, commands or data may be transmitted or received between the electronic device 101 and the external electronic device 104 via the server 108 coupled with the second network 199. Each of the external electronic devices 102 or 104 may be a device of the same type as or a different type from the electronic device 101. According to an embodiment of the disclosure, all or some of operations to be executed by the electronic device 101 may be executed at one or more external electronic devices (e.g., the external devices 102 and 104, and the server 108). For example, if the electronic device 101 needs to perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and may transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In an embodiment of the disclosure, the external electronic device 104 may include an Internet-of-things (IoT) device. The server 108 may be an intelligent server using machine learning and/or a neural network. According to an embodiment of the disclosure, the external electronic device 104 or the server 108 may be included in the second network 199. The electronic device 101 may be applied to intelligent services (e.g., smart home, smart city, smart car, or healthcare) based on 5G communication technology or IoT-related technology.

Figure 2A:
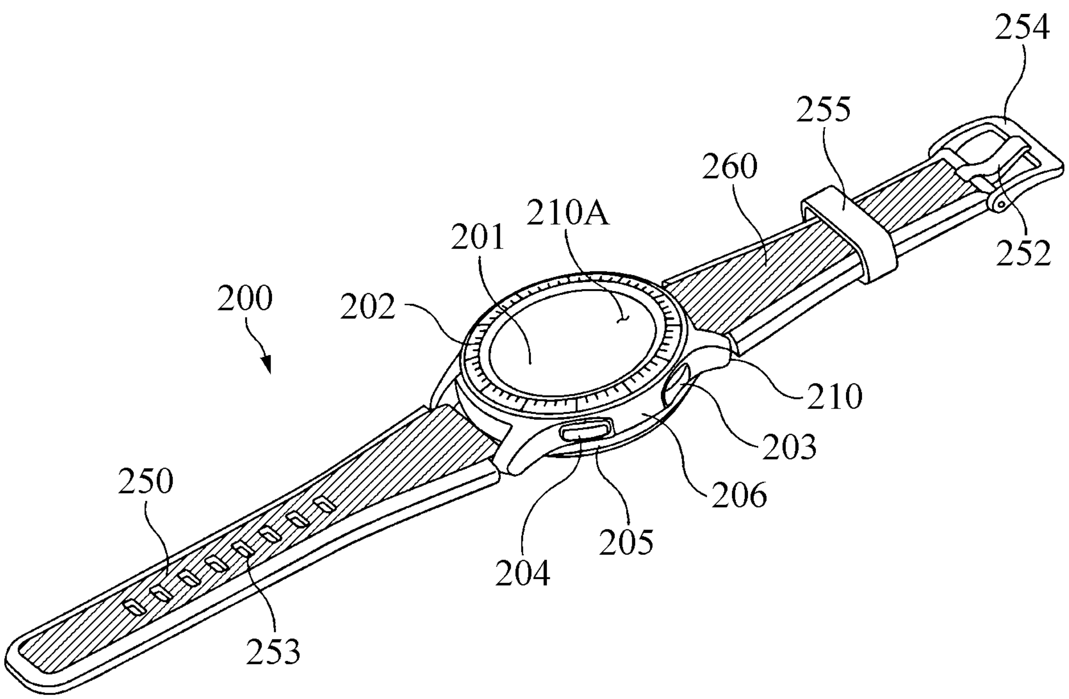
FIGS. 2A and 2B are front and rear perspective views, respectively, of an electronic device according to an embodiment of the disclosure.
Figure 2B:
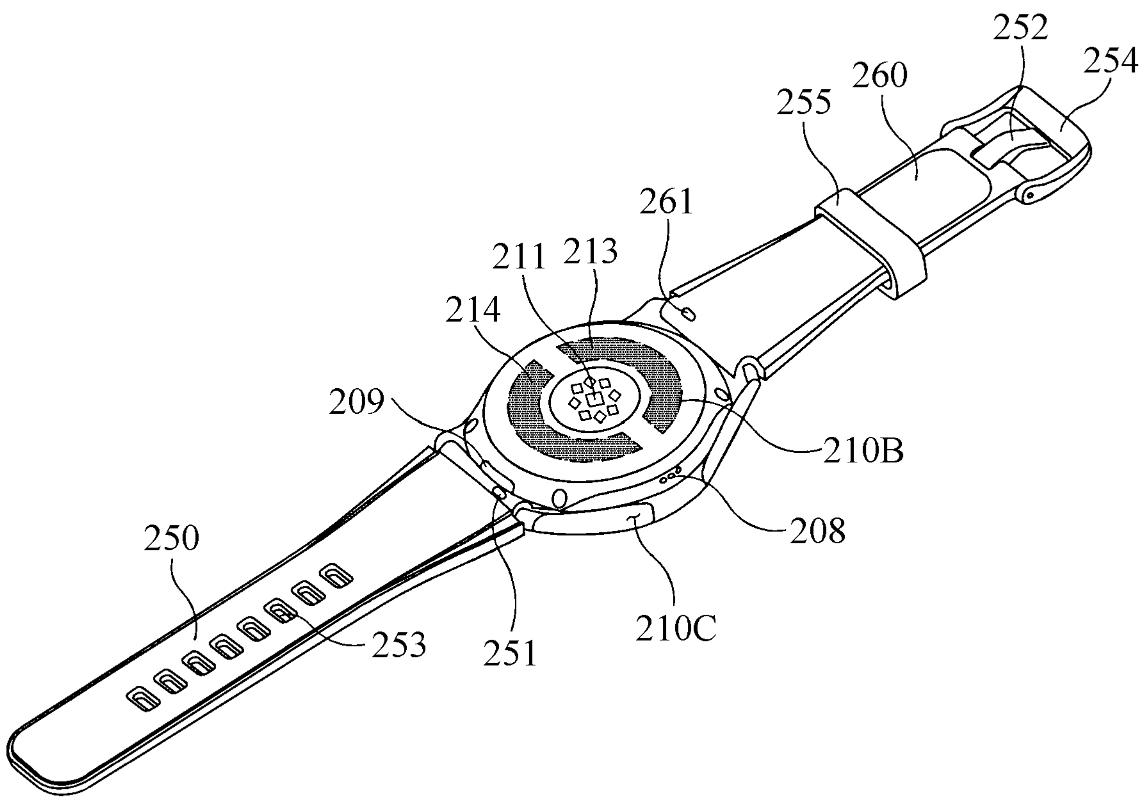

FIGS. 2A and 2B are front and rear perspective views, respectively, of an electronic device according to an embodiment of the disclosure.

Referring to FIGS. 2A and 2B, according to an embodiment of the disclosure, an electronic device 200 (e.g., the electronic device 101 of FIG. 1) may include a housing 210 including a first surface (or a front surface) 210A, a second surface (or a rear surface) 210B, and a side surface 210C surrounding a space between the first surface 210A and the second surface 210B, and fastening members 250 and 260 connected to at least a portion of the housing 210 and configured to detachably attach the electronic device 200 to a body part (e.g., a wrist, or an ankle) of a user. In an embodiment (not shown), the housing may also refer to a structure which forms a portion of the first surface 210A, the second surface 210B, and the side surface 210C of FIG. 2A. According to an embodiment of the disclosure, the first surface 210A may be formed by a front plate 201 (e.g., a glass plate or a polymer plate including various coating layers) of which at least a portion is substantially transparent. The second surface 210B may be formed by a rear plate 207 that is substantially opaque. The rear plate 207 may be formed of, for example, coated or colored glass, ceramic, polymer, metal (e.g., aluminum, stainless steel (SS), or magnesium), or a combination of at least two thereof. The side surface 210C may be coupled to the front plate 201 and the rear plate 207 and may be formed by a side bezel structure (or a "side member") 206 including a metal and/or a polymer. In an embodiment of the disclosure, the rear plate 207 and the side bezel structure 206 may be integrally formed and may include the same material (e.g., a metal material, such as aluminum). The fastening members 250 and 260 may be formed of various materials and may have various shapes. For example, the fastening members 250 and 260 may be formed of woven fabric, leather, rubber, urethane, metal, ceramic, or a combination of at least two of the aforementioned materials and may be implemented in an integrated form or with a plurality of unit links that are movable relative to each other.

According to an embodiment of the disclosure, the electronic device 200 may include at least one of a display 220 (refer to FIG. 3), audio modules 205 and 208, a sensor module 211, key input devices 202, 203, and 204, and a connector hole 209. In an embodiment of the disclosure, the electronic device 200 may not include at least one (e.g., the key input devices 202, 203, and 204, the connector hole 209, or the sensor module 211) of the components, or additionally include other components.

The display 220 may be visible through, for example, some portions of the front plate 201. The display 220 may have a shape corresponding to a shape of the front plate 201, and may have various shapes, such as a circle, an oval, or a polygon. The display 220 may be coupled to or disposed adjacent to a touch detection circuit, a pressure sensor capable of measuring an intensity (or pressure) of a touch, and/or a fingerprint sensor.

The audio modules 205 and 208 may include a microphone hole 205 and a speaker hole 208. A microphone for acquiring an external sound may be disposed in the microphone hole 205. In some embodiments of the disclosure, a plurality of microphones may be disposed to detect a direction of a sound. The speaker hole 208 may be used as an external speaker and a call receiver for calls. In an embodiment of the disclosure, the speaker hole 208 and the microphone hole 205 may be implemented as a single hole, or a speaker (e.g., a piezo speaker) may be included without the speaker hole 208.

The sensor module 211 may generate an electrical signal or a data value corresponding to an internal operating state of the electronic device 200 or an external environmental state. The sensor module 211 may include, for example, a biometric sensor module 211 (e.g., a heart rate monitor (HRM) sensor) disposed on the second surface 210B of the housing 210. The electronic device 200 may further include at least one of sensor modules (not shown), for example, a gesture sensor, a gyro sensor, an atmospheric pressure sensor, a magnetic sensor, an acceleration sensor, a grip sensor, a color sensor, an infrared (IR) sensor, a biometric sensor, a temperature sensor, a humidity sensor, or an illuminance sensor.

The sensor module 211 may include electrode areas 213 and 214 that form a portion of the surface of the electronic device 200 and a biosignal detection circuit (not shown) electrically connected to the electrode areas 213 and 214. For example, the electrode areas 213 and 214 may include a first electrode area 213 and a second electrode area 214 disposed on the second surface 210B of the housing 210. The sensor module 211 may be configured such that the electrode areas 213 and 214 obtain an electrical signal from a body part of the user, and the biosignal detection circuit detects biometric information of the user based on the electrical signal.

The key input devices 202, 203, and 204 may include a wheel key 202 disposed on the first surface 210A of the housing 210 and rotatable in at least one direction, and/or side key buttons 203 and 204 disposed on the side surface 210C of the housing 210. The wheel key 202 may have a shape corresponding to the shape of the front plate 201. In an embodiment of the disclosure, the electronic device 200 may not include some or all of the above-described key input devices 202, 203, and 204, and the key input devices 202, 203, and 204 that are not included may be implemented in other forms, such as soft keys on the display 220. The connector hole 209 may include another connector hole (not shown) that accommodates a connector (e.g., a universal serial bus (USB) connector) for transmitting and receiving power and/or data to and from an external electronic device and accommodates a connector for transmitting and receiving an audio signal to and from an external electronic device. The electronic device 200 may further include, for example, a connector cover (not shown) that covers at least a portion of the connector hole 209 and blocks infiltration of external foreign materials into the connector hole 209.

The fastening members 250 and 260 may be detachably fastened to at least a partial area of the housing 210 using locking members 251 and 261. The fastening members 250 and 260 may include one or more of a fixing member 252, a fixing member fastening hole 253, a band guide member 254, and a band fixing ring 255.

The fixing member 252 may be configured to fix the housing 210 and the fastening members 250 and 260 to a part (e.g., a wrist, an ankle, or the like) of the user's body. The fixing member fastening hole 253 may correspond to the fixing member 252 to fix the housing 210 and the fastening members 250 and 260 to the part of the user's body. The band guide member 254 may be configured to limit a range of a movement of the fixing member 252 when the fixing member 252 is fastened to the fixing member fastening hole 253, so that the fastening members 250 and 260 may be fastened to the part of the user's body in a state of being brought into close contact with the part of the user's body. The band fixing ring 255 may limit a range of a movement of the fastening member 250 and 260 in a state in which the fixing member 252 and the fixing member fastening hole 253 are fastened with each other.

Figure 3:
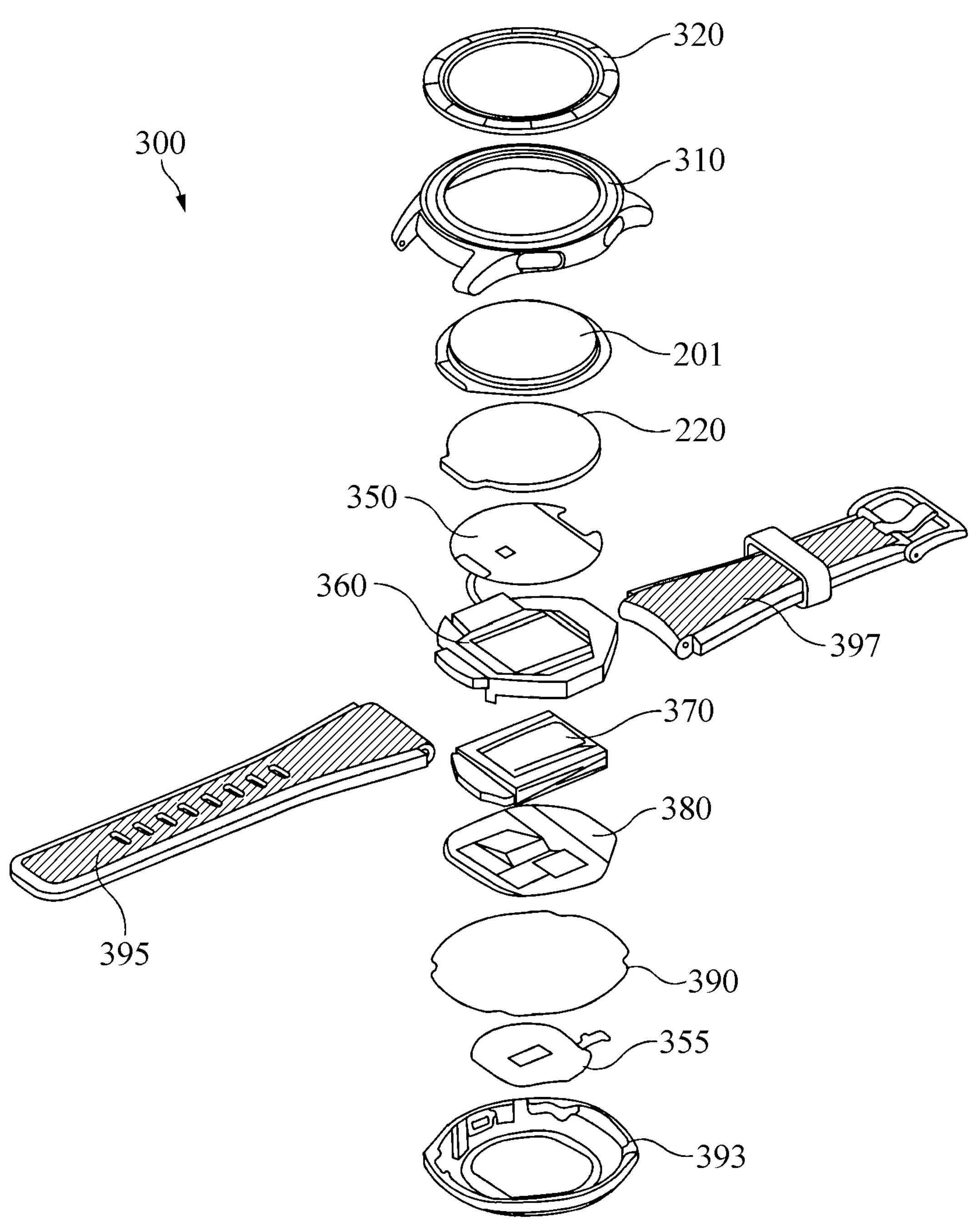
FIG. 3 is an exploded perspective view of an electronic device according to an embodiment of the disclosure.

FIG. 3 is an exploded perspective view of an electronic device according to an embodiment of the disclosure.

Referring to FIG. 3, an electronic device 300 (e.g., the electronic device 101 of FIG. 1 or the electronic device 200 of FIGS. 2A and 2B) may include a side bezel structure 310, a wheel key 320, a front plate 201, a display 220, a first antenna 350, a second antenna 355, a support member 360 (e.g., a bracket), a battery 370, a PCB 380, a sealing member 390, a rear plate 393, and fastening members 395 and 397. At least one of the components of the electronic device 300 may be the same as or similar to at least one of the components of the electronic device 100 of FIG. 1, or the electronic device 200 of FIGS. 2A and 2B, and a repeated description thereof will be omitted hereinafter.

The support member 360 may be disposed inside the electronic device 300 and connected to the side bezel structure 310, or may be integrally formed with the side bezel structure 310. The support member 360 may be formed of, for example, a metal material and/or a non-metal material (e.g., polymer). The display 220 may be connected to one surface of the support member 360, and the PCB 380 may be connected to another surface of the support member 360.

The PCB 380 may be provided with a processor, a memory, and/or an interface mounted thereon. The processor may include, for example, one or more of a CPU, an AP, a GPU, a sensor processor, or a CP. The memory may include, for example, a volatile memory or a non-volatile memory. The interface may include, for example, an HDMI, a USB interface, an SD card interface, or an audio interface. For example, the interface may electrically or physically connect the electronic device 300 to an external electronic device, and may include a USB connector, an SD card/multimedia card (MMC) connector, or an audio connector.

The battery 370, which is a device for supplying power to at least one component of the electronic device 300, may include, for example, a non-rechargeable primary battery, a rechargeable secondary battery, or a fuel cell. For example, at least a portion of the battery 370 may be disposed on substantially the same plane as the PCB 380. The battery 370 may be disposed integrally inside the electronic device 300, or disposed detachably from the electronic device 300.

The first antenna 350 may be disposed between the display 220 and the support member 360. The first antenna 350 may include, for example, a near-field communication (NFC) antenna, a wireless charging antenna, and/or a magnetic secure transmission (MST) antenna. For example, the first antenna 350 may perform short-range communication with an external device, wirelessly transmit and receive power used for charging, or transmit a magnetism-based signal including a short-range communication signal or payment data. In an embodiment of the disclosure, an antenna structure may be formed by a portion of the side bezel structure 310 and/or the support member 360, or a combination thereof.

The second antenna 355 may be disposed between the PCB 380 and the rear plate 393. The second antenna 355 may include, for example, an NFC antenna, a wireless charging antenna, and/or an MST antenna. For example, the second antenna 355 may perform short-range communication with an external device, wirelessly transmit and receive power used for charging, or transmit a magnetism-based signal including a short-range communication signal or payment data. In an embodiment of the disclosure, an antenna structure may be formed by a portion of the side bezel structure 310 and/or the rear plate 393, or a combination thereof.

The sealing member 390 may be disposed between the side bezel structure 310 and the rear plate 393. The sealing member 390 may be configured to prevent and/or reduce moisture and foreign materials from being introduced into a space surrounded by the side bezel structure 310 and the rear plate 393 from the outside.

The electronic devices according to an embodiment may be various types of electronic devices. The electronic device may include, for example, a portable communication device (e.g., a smartphone), a computer device, a portable multimedia device, a portable medical device, a camera, a wearable device, or a home appliance device. According to an embodiment of the disclosure, the electronic device is not limited to those described above.

It should be appreciated that embodiments of the disclosure and the terms used therein are not intended to limit the technological features set forth herein to particular embodiments and include various changes, equivalents, or replacements for a corresponding embodiment. In connection with the description of the drawings, like reference numerals may be used for similar or related components. It is to be understood that a singular form of a noun corresponding to an item may include one or more of the things, unless the relevant context clearly indicates otherwise. As used herein, "A or B", "at least one of A and B", "at least one of A or B", "A, B or C", "at least one of A, B and C", and "at least one of A, B, or C," each of which may include any one of the items listed together in the corresponding one of the phrases, or all possible combinations thereof. Terms, such as "$1^{st}$", "$2^{nd}$", or "first" or "second" may simply be used to distinguish the component from other components in question, and do not limit the components in other aspects (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., by wire), wirelessly, or via a third element.

As used in connection with an embodiment of the disclosure, the term "module" may include a unit implemented in hardware, software, or firmware, and may interchangeably be used with other terms, for example, "logic," "logic block," "part," or "circuitry." A module may be a single integral component, or a minimum unit or part thereof, adapted to perform one or more functions. For example, according to an embodiment of the disclosure, the module may be implemented in a form of an application-specific integrated circuit (ASIC).

An embodiment as set forth herein may be implemented as software (e.g., the program 140) including one or more instructions that are stored in a storage medium (e.g., an internal memory 136 or an external memory 138) that is readable by a machine (e.g., the electronic device 101 of FIG. 1). For example, a processor (e.g., the processor 120) of the machine (e.g., the electronic device 101) may invoke at least one of the one or more instructions stored in the storage medium, and execute it. This allows the machine to be operated to perform at least one function according to the at least one instruction invoked. The one or more instructions may include a code generated by a compiler or a code executable by an interpreter. The machine-readable storage medium may be provided in the form of a non-transitory storage medium. Here, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment of the disclosure, a method according to an embodiment of the disclosure may be included and provided in a computer program product. The computer program product may be traded as a product between a seller and a buyer. The computer program product may be distributed in the form of a machine-readable storage medium (e.g., a compact disc read-only memory (CD-ROM)), or be distributed (e.g., downloaded or uploaded) online via an application store (e.g., PlayStore™), or between two user devices (e.g., smartphones) directly. If distributed online, at least part of the computer program product may be temporarily generated or at least temporarily stored in the machine-readable storage medium, such as memory of the manufacturer's server, a server of the application store, or a relay server.

According to an embodiment of the disclosure, each component (e.g., a module or a program) of the above-described components may include a single entity or multiple entities, and some of the multiple entities may be separately disposed in different components. According to an embodiment of the disclosure, one or more of the above-described components may be omitted, or one or more other components may be added. Alternatively or additionally, a plurality of components (e.g., modules or programs) may be integrated into a single component. In such a case, according to an embodiment of the disclosure, the integrated component may still perform one or more functions of each of the plurality of components in the same or similar manner as they are performed by a corresponding one of the plurality of components before the integration. According to an embodiment of the disclosure, operations performed by the module, the program, or another component may be carried out sequentially, in parallel, repeatedly, or heuristically, or one or more of the operations may be executed in a different order or omitted, or one or more other operations may be added.

Figure 4:
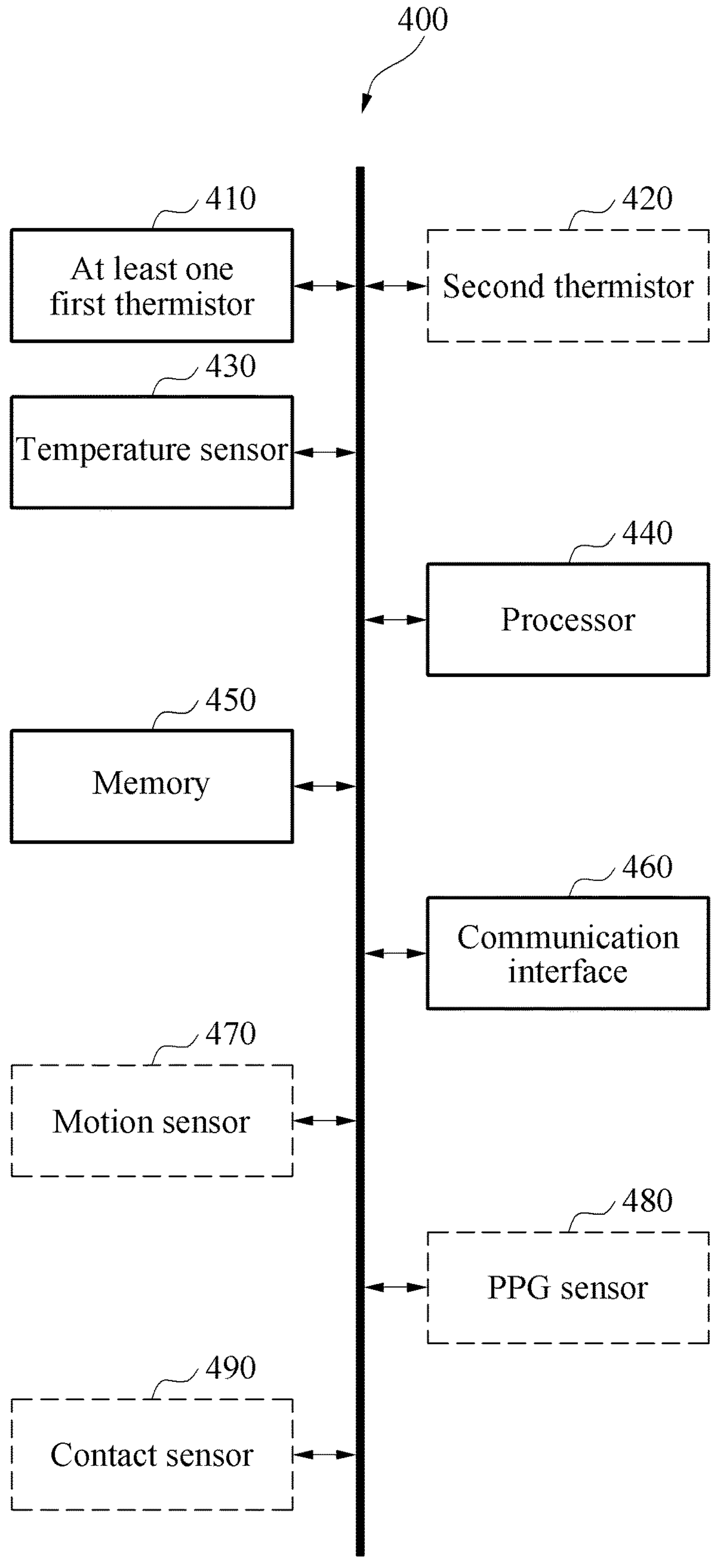
FIG. 4 is a block diagram illustrating a configuration of a wearable electronic device according to an embodiment of the disclosure.

FIG. 4 is a block diagram illustrating a configuration of a wearable electronic device according to an embodiment of the disclosure.

Referring to FIG. 4, a wearable electronic device 400 (e.g., the electronic devices 101 and 104 of FIG. 1, the electronic device 200 of FIGS. 2A and 2B, or the electronic device 300 of FIG. 3) according to an embodiment may include at least one first thermistor 410, a second thermistor 420, a temperature sensor 430, a processor 440 (e.g., the processor 120 of FIG. 1), a memory 450 (e.g., the memory 130 of FIG. 1), and a communication interface 460 (e.g., the communication module 190 of FIG. 1). In addition, the wearable electronic device 400 may further include a motion sensor 470, a photoplethysmogram (PPG) sensor 480, and a contact sensor 490. The at least one first thermistor 410, the second thermistor 420, the temperature sensor 430, the motion sensor 470, the PPG sensor 480, and the contact sensor 490 may be included in, for example, the sensor module 176 of FIG. 1, or the sensor module 211 of FIG. 2.

A thermistor may be a semiconductor formed of various metal oxides, and may exhibit a property that a resistance decreases as a temperature increases, unlike general metals. In an embodiment of the disclosure, based on the property of the thermistor in which the resistance decreases as the temperature increases, the temperature may be measured by converting a thermal signal into an electrical signal. A thermistor (e.g., the at least one first thermistor 410 and/or the second thermistor 420) according to an embodiment may be a sensor used to measure a temperature of a component included in the wearable electronic device 400, rather than measuring a body temperature. The at least one first thermistor 410 and the second thermistor 420 may measure a temperature in a wider range than that of the temperature sensor 430 for measuring a body temperature, but may have a poor accuracy or resolution.

The at least one first thermistor 410 may be disposed adjacent to positions of different heat generation sources (e.g., electronic components or electronic elements) of the wearable electronic device 400, to detect a temperature change of internal elements of the wearable electronic device 400. The internal elements may include, for example, at least one of an AP (e.g., the processor 120 of FIG. 1, and an AP 605 of FIG. 6C), a battery (e.g., the battery 189 of FIG. 1, and a battery 602 of FIG. 6C), or a CP (e.g., a CP 604 of FIG. 6C), and may further include various elements that generate heat. Heat generation positions different from each other may be positions adjacent to the battery 602, the CP 604, and the AP 605.

The AP 605 may generate heat when an operation of an application, such as processing according to an execution of an application or a graphic operation, is performed. The battery 602 may generate heat during wired or wireless charging, for example. The CP 604 may generate heat, for example, during signal amplification for a wireless communication. The at least one first thermistor 410 may be disposed near a heat generation source, for example, the battery 602, the CP 604, and the AP 605, included in the wearable electronic device 400.

The at least one first thermistor 410 may be used to prevent damage to a component or to prevent a user from being burnt, by directly detecting a temperature rise of the internal elements of the wearable electronic device 400. The wearable electronic device 400 may estimate an internal temperature of the wearable electronic device 400 based on a temperature rise of the heat generation source detected by the at least one first thermistor 410, and/or may control a body temperature detection operation.

The at least one first thermistor 410 may be, for example, a single thermistor, or a plurality of thermistors. Alternatively, the at least one first thermistor 410 may be a combination of thermistors disposed at different positions in the wearable electronic device 400.

The at least one first thermistor 410 may continue to monitor the temperature rise of the internal elements independently of driving of the temperature sensor 430. A monitoring result of the at least one first thermistor 410 may trigger the temperature sensor 430 to calculate a body temperature of a user.

The second thermistor 420 may estimate a skin temperature trend of a user outside the wearable electronic device 400. The skin temperature trend may correspond to a skin temperature standardized to a body temperature value. Since the second thermistor 420 is located outside the wearable electronic device 400 and operates at all times, the processor 440 may drive the second thermistor 420 in advance to determine a situation before the temperature sensor 430 starts to detect a body temperature.

For example, when the wearable electronic device 400 is of a watch type, the second thermistor 420 may be disposed on a portion in contact with a user's skin, that is, on a glass surface of a bottom portion of the watch and may estimate an external temperature of the wearable electronic device 400, for example, a user's skin temperature trend. In this example, the skin temperature trend estimated by the second thermistor 420 may correspond to rough information. For example, the processor 440 may determine that it is difficult to measure the body temperature due to internal heat generation detected by the at least one first thermistor 410, or may determine, in advance, that a temperature detected by the second thermistor 420 outside the wearable electronic device 400 is out of a temperature range (e.g., a range of about 30 to 45° C.), in which it is easy to measure a body temperature using the temperature sensor 430, because the detected temperature is extremely high or low. The processor 440 may trigger the temperature sensor 430 to measure a body temperature value based on a result of determination by the temperature detected by the at least one first thermistor 410 and/or the second thermistor 420.

Since the second thermistor 420 estimates a temperature trend of a user's skin surface, the second thermistor 420 may also be referred to as a "surface thermistor."

The second thermistor 420 may be used to estimate a temperature of the PPG sensor 480 that substantially measures biometric information. Since the PPG sensor 480 is located adjacent to a body outside the wearable electronic device 400 and the second thermistor 420 is also located adjacent to a skin outside the wearable electronic device 400, the second thermistor 420 may be located outside to measure an effect of a user's skin temperature unlike the at least one first thermistor 410.

Unlike the at least one first thermistor 410 near the internal elements of the wearable electronic device 400, the second thermistor 420 may estimate an external temperature. The second thermistor 420 may be in contact with a skin and may be used to estimate a skin temperature, that is, a skin temperature trend. Although the skin temperature is a type of body temperature, the skin temperature may correspond to a temperature corresponding to a portion in contact with a sensor, unlike a body temperature used to detect general heat. Accordingly, the skin temperature may be different from the body temperature used to detect whether a fever is caused by, for example, a disease. The body temperature may be directly measured by placing a sensor on a body part of which a body temperature may be estimated, for example, a forehead, a mouth, or an axilla, or may be indirectly estimated through a skin temperature.

An arrangement position of the at least one first thermistor 410 and an arrangement position of the second thermistor 420 in the wearable electronic device 400 will be described with reference to FIGS. 6A, 6B, and 6C below.

The temperature sensor 430, which is a sensor used to measure a temperature of a body, may measure, for example, a temperature of a body part in contact with the temperature sensor 430. The temperature sensor 430 may be, for example, an IR-type non-contact temperature sensor, but is not limited thereto.

A body temperature sensor may measure a temperature of a designated body part, such as an axilla, a mouth, the inside of an ear, and/or a forehead, in an authenticated manner according to rules prescribed by the medical community, and may provide a unified body temperature standard based on the measured temperature. The temperature sensor 430 may fail to represent a body temperature measured by a medical device because the temperature sensor 430 measures a temperature of a distal part of a body, such as a skin of a wrist. Therefore, in an embodiment of the disclosure, the processor 440 may estimate a body temperature by comparing a skin temperature value measured on a wrist through various clinical tests to a value of a body temperature sensor measured based on an existing predetermined body part and output the body temperature.

The temperature sensor 430 may not be driven frequently due to a relatively large amount of current to be consumed despite a high accuracy. However, since the at least one first thermistor 410 and the second thermistor 420 are driven at all times, it may be easy to track a trend.

According to an embodiment of the disclosure, the temperature sensor 430 and the processor 440 may also be configured as a single temperature detection module.

A method by which the temperature sensor 430 calculates a body temperature will be described with reference to FIG. 5 below.

The processor 440 may determine whether an internal temperature by the internal elements in the wearable electronic device 400 is within a reference temperature range (e.g., a range of about 16 to 40° C.) that does not have an influence on a calculation of a body temperature of a user, based on a measured value of the at least one first thermistor 410.

The contact sensor 490 may detect whether a user is in contact with the wearable electronic device 400. In an embodiment of the disclosure, the contact sensor 490 may be, for example, at least one of a proximity sensor, a touch (grip) sensor, or an atmospheric pressure sensor. In an embodiment of the disclosure, the proximity sensor may detect whether an external object (e.g., a user) wears the wearable electronic device 400, using an optical scheme, a radio frequency (RF) scheme, or a sound wave scheme. For example, a plurality of proximity sensors using the optical scheme may be arranged according to arrangement positions of the proximity sensors.

If it is determined by the contact sensor 490 that the user wears the wearable electronic device 400, the processor 440 may determine whether the internal temperature is within the reference temperature range based on a measured value of the at least one first thermistor 410. The wearable electronic device 400 may determine a heat generation level of the at least one first thermistor 410, and may identify a cause of heat generation according to a predetermined event in each of the at least one first thermistor 410.

The wearable electronic device 400 may calculate a representative value K therm of temperatures of the internal elements based on the measured value of the at least one first thermistor 410, and may determine whether the representative value K therm is within the reference temperature range. For example, if the at least one first thermistor 410 senses a temperature AP Therm of heat generated by an AP, a temperature Batt Therm of heat generated by a battery, and a temperature CP Therm of heat generated by a CP, the wearable electronic device 400 may calculate a representative value K therm of internal temperatures as, for example, a value of "k*(AP Therm+Batt Therm+CP Therm)/3." In this example, k may correspond to a compensation coefficient of the internal temperature of the wearable electronic device 400.

According to an embodiment of the disclosure, the wearable electronic device 400 may calculate the representative value K therm by assigning different weights for each measured value of the at least one first thermistor 410. For example, the wearable electronic device 400 may assign a weight of "0.4" to each of the temperature AP Therm of the heat generated by the AP and the temperature Batt Therm of the heat generated by the battery, may assign a weight of "0.2" to the temperature CP Therm of the heat generated by the CP, and may calculate the representative value K therm of the internal temperatures. Weights corresponding to the respective internal elements may be changed by, for example, a surrounding environment, a user setting, or an application setting, however, the embodiments are not limited thereto.

The wearable electronic device 400 may analyze a heat generation state according to heat generation levels of the internal elements, and set a time (referred to as a "reconfirmation time") used to reduce each of temperatures of the internal elements to a temperature (e.g., a temperature of about 16 to 40° C.) at which each of the internal elements is stable.

For example, when the representative value K therm is out of the reference temperature range, the processor 440 may remeasure a value of the at least one first thermistor 410 after the reconfirmation time used for a temperature decrease for each of the temperatures of the internal elements elapses. The processor 440 may determine whether the remeasured value of the at least one first thermistor 410 is within the reference temperature range. A method by which the processor 440 determines whether the internal temperature of the wearable electronic device 400 is within the reference temperature range will be described with reference to FIG. 8 below.

If it is determined that the internal temperature is within the reference temperature range, the processor 440 may determine a user state index (hereinafter, referred to as a "UI") indicating whether the user is in a state in which the body temperature is measurable, based on the measured value of the second thermistor 420. A detection result of each of the motion sensor 470 and the PPG sensor 480 may be further used to determine the UI.

The motion sensor 470 may detect a motion of the user. The motion sensor 470 may include, but is not limited to, for example, an acceleration sensor, a gyro sensor, and/or a proximity sensor. The acceleration sensor may measure an acceleration or a strength of a shock of a moving object. The acceleration sensor may measure, for example, a moving speed of X, Y, and Z coordinates corresponding to a location of a user. The gyro sensor may measure a change in an orientation of an object, that is, an angular velocity, using a property that a gyroscope always maintains an initially set direction regardless of a rotation of the earth. The proximity sensor may detect a presence of a nearby object without a physical contact. The proximity sensor may emit an electromagnetic field or an electromagnetic wave (e.g., infrared rays), and may detect a position of an object approaching a sensor by retrieving the emitted electromagnetic field and a returned signal. Since the proximity sensor detects a position, the proximity sensor may also be referred to as a "position sensor" or a "displacement sensor."

The PPG sensor 480 may detect a variation in a heart rate of a user. A pulse wave may be obtained by recognizing, as a waveform, a change in a volume of a blood vessel when a heart circulates blood, and a sensor for monitoring the change in the volume of the blood vessel may be called the "PPG sensor 480." For example, if a heart rate is measured using the PPG sensor 480, a photoelectric pulse wave scheme may be used. PPG sensors used in the photoelectric pulse wave scheme may include, for example, a transmission-type PPG sensor and a reflection-type PPG sensor, based on a measurement scheme. The transmission-type PPG sensor may measure a pulse wave by irradiating infrared rays and red light to a surface of a human body, and measuring a change in a blood flow rate that changes according to pulsation of a heart as a variation in light passing through the human body. The transmission-type PPG sensor may be used in a portion through which light easily passes, such as a fingertip or an earlobe. The reflection-type PPG sensor may irradiate infrared rays, red light, or green light with a wavelength of around 550 nanometers (nm) to a living body, and may measure light reflected from the inside of the living body using a photodiode or a phototransistor. Since arterial blood has a characteristic of absorbing incident light due to oxidized hemoglobin included in the arterial blood, the reflection-type PPG sensor may measure a PPG signal by detecting a blood flow rate (change in a volume of a blood vessel) that changes according to the pulsation of the heart, in a time series. In addition, since the reflection-type PPG sensor measures reflected light, the reflection-type PPG sensor may measure pulse waves of all body parts to be measured, unlike the transmission-type PPG sensor.

If it is determined that the internal temperature is within the reference temperature range, the processor 440 may estimate a skin temperature trend of the user wearing the wearable electronic device 400, based on the measured value of the second thermistor 420. A method by which the processor 440 estimates the skin temperature trend will be described with reference to FIG. 10 below.

The processor 440 may determine the UI based on at least one of the motion of the user detected by the motion sensor 470, a variation in the heart rate of the user detected by the PPG sensor 480, or the skin temperature trend of the user estimated by the second thermistor 420. A method by the processor 440 determines the UI will be described with reference to FIG. 9 below.

The processor 440 may measure the body temperature of the user by adjusting the body temperature measurement period based on the UI. For example, the processor 440 may reduce the body temperature measurement period when the UI is similar to an index indicating an unstable state, and may increase the body temperature measurement period when the UI is similar to an index indicating a stable state. A method by which the processor 440 adjusts the body temperature measurement period will be described with reference to FIG. 11 below.

According to an embodiment of the disclosure, the processor 440 may correct a body temperature of the user acquired according to the body temperature measurement period using the temperature sensor 430, based on the measured value of the second thermistor 420. A method by which the processor 440 corrects the body temperature of the user will be described with reference to FIG. 13 below.

The processor 440 may execute a program and control the wearable electronic device 400. A code of the program executed by the processor 440 may be stored in the memory 450.

The memory 450 may store a signal or data received through the communication interface 460 and/or the user's body temperature calculated and/or corrected by the processor 440.

The memory 450 may store a variety of information generated in a processing process of the processor 440 described above. In addition, the memory 450 may store a variety of data and programs. The memory 450 may include, for example, a volatile memory or a non-volatile memory. The memory 450 may include a high-capacity storage medium, such as a hard disk to store a variety of data.

The communication interface 460 may output the user's body temperature calculated and/or corrected by the processor 440 to the outside of the wearable electronic device 400. The communication interface 460 may receive a signal detected outside the wearable electronic device 400, or other data.

In addition, the processor 440 may perform at least one method that will be described with reference to FIGS. 5, 6A, 6B, 6C, and 7 to 14 below or a scheme corresponding to the at least one method. The processor 440 may be a hardware-implemented wearable electronic device having a circuit that is physically structured to execute desired operations. For example, the desired operations may include codes or instructions included in a program. The hardware-implemented wearable electronic device may include, for example, a microprocessor, a CPU, a GPU, a processor core, a multi-core processor, a multiprocessor, an ASIC, a field-programmable gate array (FPGA), or an NPU.

Figure 5:
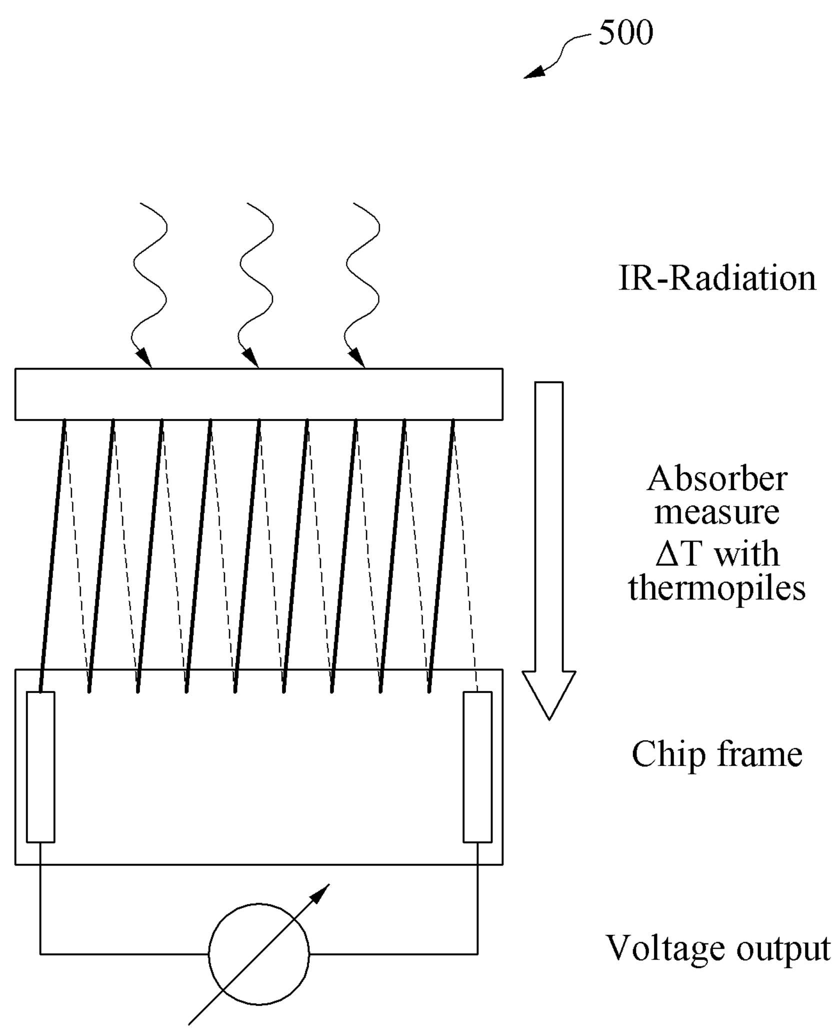
FIG. 5 is a diagram illustrating a measurement method of a temperature sensor according to an embodiment of the disclosure.

FIG. 5 is a diagram illustrating a measurement method of a temperature sensor according to an embodiment of the disclosure.

Referring to FIG. 5, a structure of a non-contact IR temperature sensor 500 (e.g., the temperature sensor 430 of FIG. 4) according to an embodiment is illustrated.

All objects may have temperatures greater than or equal to absolute zero (0 K) corresponding to −273.15° C. and −459.67° F., and may radiate electromagnetic waves of a wavelength corresponding to the temperatures. For example, if a temperature increases, a wavelength of a radiated electromagnetic wave may decrease, and an amount of radiant energy may increase.

The non-contact IR temperature sensor 500 may form a contact point with two different materials of internal thermopiles on one side thereof, and may form a thermocouple with an open structure on another side thereof, to detect a temperature using a Seebeck effect in which an electromotive force is generated in proportion to a magnitude of a temperature difference between the contact point and the opened structure. Although the overall structure of the non-contact IR temperature sensor 500 is a closed structure, two contact points may be in an open form of being spaced apart from each other when an electromotive force generated by a temperature difference between the two contact points is measured.

The non-contact IR temperature sensor 500 may estimate energy emitted from a user's skin based on the Stefan-Boltzmann formula as shown in Equation 1 below.

$$j = \varepsilon\sigma T^4 \quad \text{Equation 1}$$

In Equation 1, j denotes an irradiance ($W/m^2$), and & denotes an emissivity (~0.9). In addition, $\sigma(W/m^2K^4)$ may correspond to a Stefan-Boltzmann constant.

The Stefan-Boltzmann formula may correspond to a law with an amount of energy radiated from a perfect black body (i.e., a radiator) as a function of an absolute temperature, and energy W radiated per unit time from an area of the perfect black body may be proportional to the fourth power of the absolute temperature T.

The non-contact IR temperature sensor 500 may calculate a body temperature of a user using the Stefan-Boltzmann formula, based on a temperature change of internal elements of a wearable electronic device (e.g., the electronic devices 101 and 104 of FIG. 1, the electronic device 200 of FIGS. 2A and 2B, the electronic device 300 of FIG. 3, or the wearable electronic device 400 of FIG. 4) detected by at least one first thermistor (e.g., the at least one thermistor 410 of FIG. 4), and based on a skin temperature trend of the user estimated by a second thermistor (e.g., the second thermistor 420 of FIG. 4) outside the wearable electronic device 400.

Figure 6A:
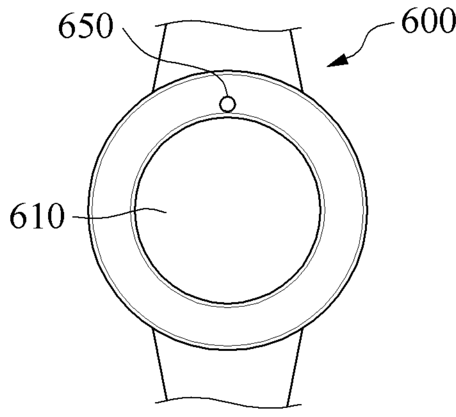
FIGS. 6A, 6B, and 6C are diagrams illustrating a configuration of a wearable electronic device according to an embodiment of the disclosure.
Figure 6B:
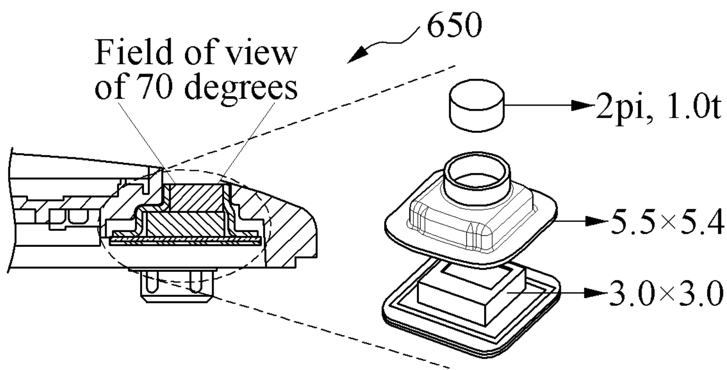
Figure 6C:
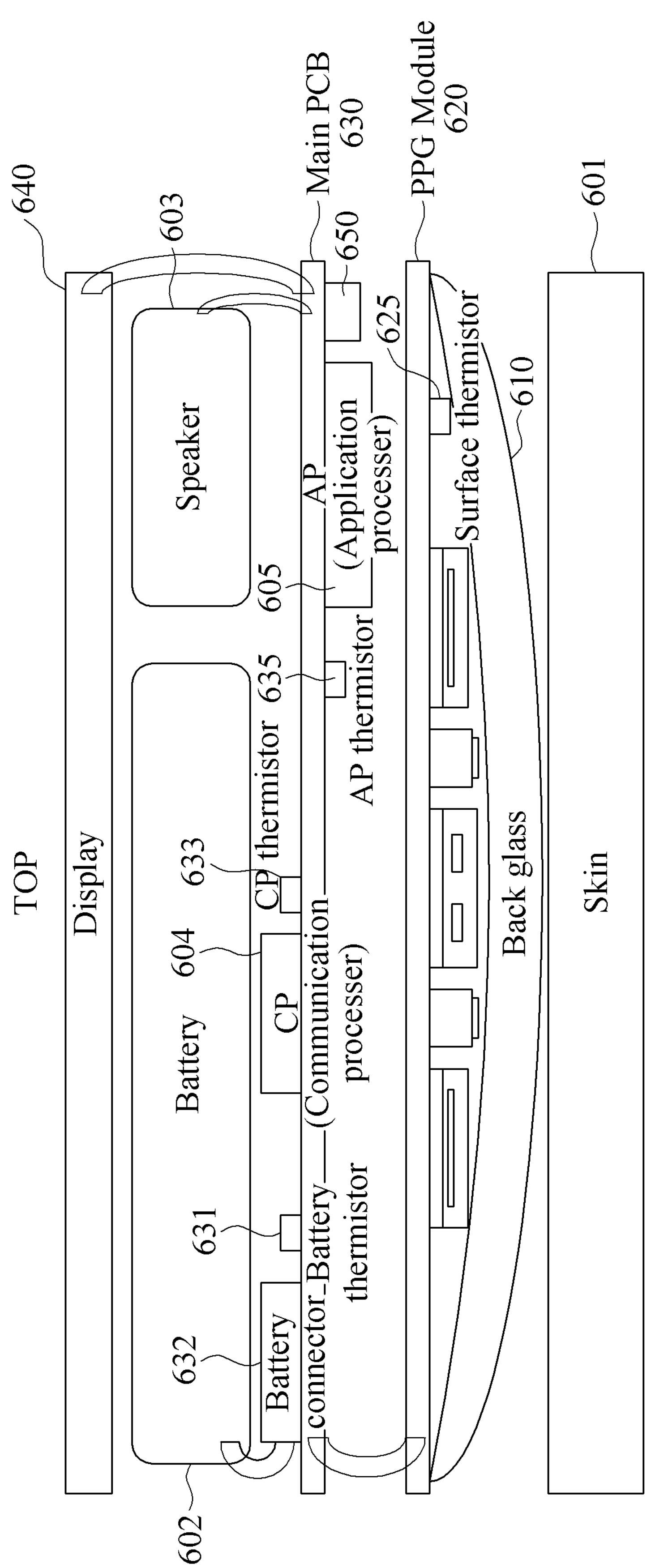

FIGS. 6A, 6B, and 6C illustrate a configuration of a wearable electronic device according to various embodiments of the disclosure.

Referring to FIG. 6A, it illustrates a plan view of a wearable electronic device 600 (e.g., the electronic devices 101 and 104 of FIG. 1, the electronic device 200 of FIGS. 2A and 2B, the electronic device 300 of FIG. 3, or the wearable electronic device 400 of FIG. 4) according to an embodiment. Referring to FIG. 6B, it illustrates an enlarged cross-sectional view of a temperature sensor 650 according to an embodiment. In addition, Referring to FIG. 6C, it illustrates a side perspective view of an arrangement structure of internal elements within a housing of the wearable electronic device 600 according to an embodiment when viewed from a side.

The wearable electronic device 600 may include the battery 602 (e.g., the battery 189 of FIG. 1), a speaker 603, the CP 604, the AP 605 (e.g., the processor 120 of FIG. 1), a back glass 610 in contact with a skin 601 of a user, a PPG module 620, a surface thermistor 625, a main PCB 630, a battery thermistor 631, a CP thermistor 633, an AP thermistor 635, a front display 640, and a temperature sensor 650 (e.g., the temperature sensor 430 of FIG. 4, and the non-contact IR temperature sensor 500 of FIG. 5).

The CP 604 and the AP 605 may be disposed on the main PCB 630. The battery thermistor 631, the CP thermistor 633, and the AP thermistor 635 may be disposed on the main PCB 630, and the surface thermistor 625 may be disposed on the PPG module 620. The battery thermistor 631, the CP thermistor 633, and the AP thermistor 635 may correspond to, for example, the at least one first thermistor 410 of FIG. 4 described above, and the surface thermistor 625 may correspond to, for example, the second thermistor 420 of FIG. 4 described above.

The battery thermistor 631 may be disposed adjacent to a battery connector 632 that connects the battery 602 and the main PCB 630, to detect heat generated during charging of the battery 602.

The CP thermistor 633 may be disposed adjacent to the CP 604 to detect heat generated during signal amplification for a wireless communication in the CP 604.

The AP thermistor 635 may be disposed adjacent to the AP 605 to detect heat generated when various application operations are performed in the AP 605.

The AP 605 may calculate a body temperature using a skin temperature of a measurement body part detected by the surface thermistor 625 and an internal temperature of a sensor detected by the battery thermistor 631, the CP thermistor 633, and the AP thermistor 635. The AP 605 may correct a user's body temperature acquired through the temperature sensor 650 to a body temperature value within a typical body temperature range of a person using a measured value of the surface thermistor 625.

In an embodiment of the disclosure, an example of using three first thermistors, for example, the battery thermistor 631, the CP thermistor 633, and the AP thermistor 635, and a single second thermistor, for example, the second thermistor 625, has been described above, however, the embodiments are not limited thereto. A number of first thermistors and a number of second thermistors may vary depending to embodiments.

Figure 7:
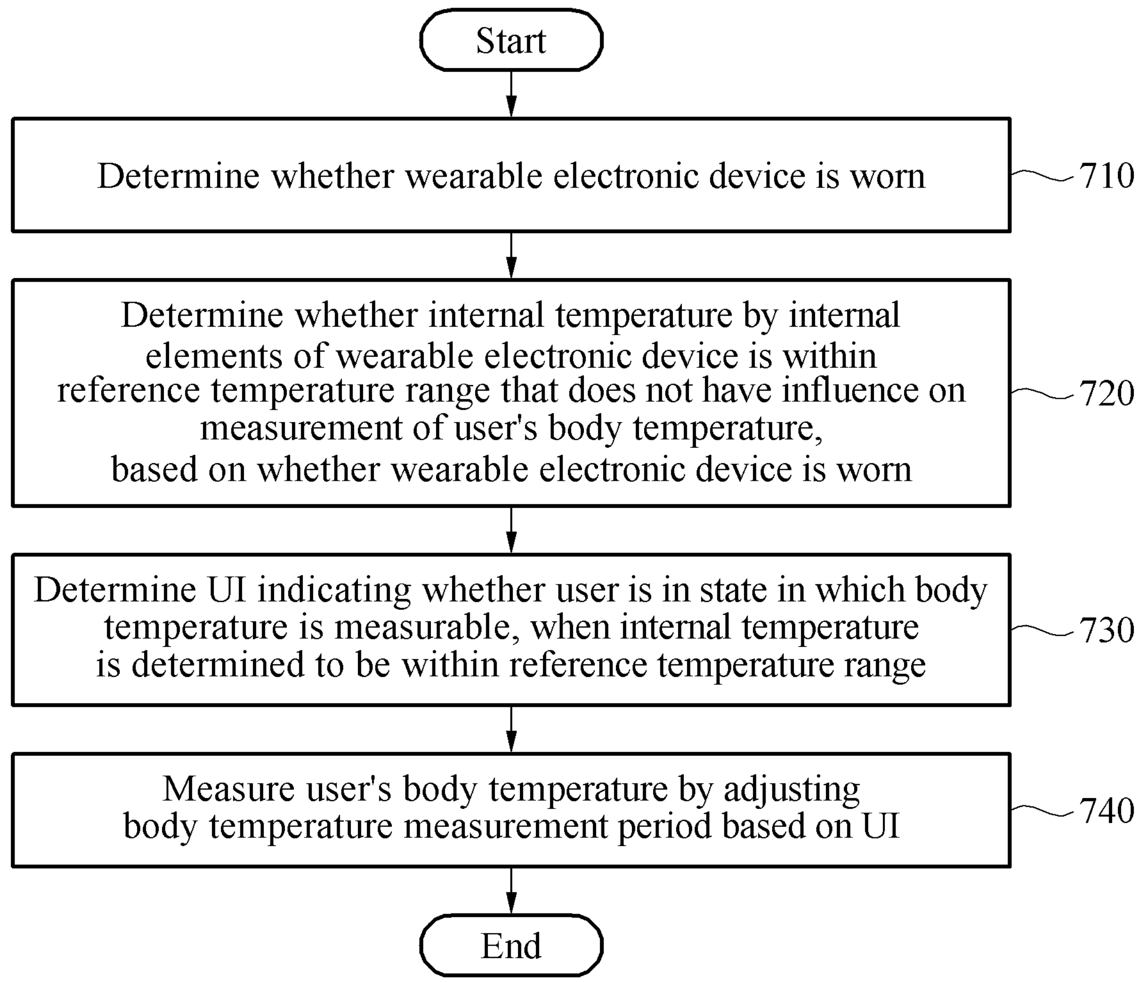
FIG. 7 is a flowchart illustrating a method of operating a wearable electronic device according to an embodiment of the disclosure.

FIG. 7 is a flowchart illustrating a method of operating a wearable electronic device according to an embodiment of the disclosure. In the following embodiments of the disclosure, operations may be performed sequentially, but are not necessarily performed sequentially. For example, the order of the operations may be changed and at least two of the operations may be performed in parallel.

Referring to FIG. 7, a wearable electronic device (e.g., the electronic devices 101 and 104 of FIG. 1, the electronic device 200 of FIGS. 2A and 2B, the electronic device 300 of FIG. 3, the wearable electronic device 400 of FIG. 4, and/or the wearable electronic device 600 of FIG. 6A) according to an embodiment may measure a body temperature of a user through operations 710 to 740.

In operation 710, the wearable electronic device 400 may determine whether the wearable electronic device 400 is worn, that is, whether the user is wearing the wearable electronic device 400. The wearable electronic device 400 may determine whether the user is wearing the wearable electronic device 400, using a proximity sensor or a contact sensor (e.g., the contact sensor 490 of FIG. 4) configured to detect whether the user is in contact with the wearable electronic device 400. In an example, if it is determined that the user is wearing the wearable electronic device 400, the wearable electronic device 400 may set a state variable W of the user to "1." In another example, if it is determined that the user is not wearing the wearable electronic device 400, the wearable electronic device 400 may set the state variable W to "0."

In operation 720, the wearable electronic device 400 may determine whether an internal temperature by internal elements of the wearable electronic device 400 is within a reference temperature range (e.g., a range of about 16 to 40° C.) that does not have an influence on a measurement of the body temperature, based on whether the wearable electronic device 400 is worn determined in operation 710. In an example, when the state variable W is set to "1," the wearable electronic device 400 may measure the internal temperature by the internal elements and determine whether the internal temperature is within the reference temperature range. In another example, when the state variable W is set to "0," the wearable electronic device 400 may not measure the internal temperature by the internal elements.

The wearable electronic device 400 may determine whether the internal temperature by the internal elements is within the reference temperature range, based on a measured value of at least one first thermistor (e.g., the at least one first thermistor 410 of FIG. 4, and the battery thermistor 631, the CP thermistor 633, and the AP thermistor 635 of FIG. 6C) arranged in different heat generation positions in the wearable electronic device 400 to detect a temperature change of the internal elements. The internal elements may include, but are not necessarily limited to, various heat-generating elements, such as an AP, a battery, and a CP.

The wearable electronic device 400 may determine a heat generation level of the at least one first thermistor 410, and may identify a cause of heat generation according to a predetermined event in each of the at least one first thermistor 410. The wearable electronic device 400 may calculate a representative value K therm of temperatures of the internal elements based on the measured value of the at least one first thermistor 410, and may determine whether the representative value K therm is within the reference temperature range. According to an embodiment of the disclosure, the wearable electronic device 400 may calculate the representative value K therm by assigning different weights for each measured value of the at least one first thermistor 410.

For example, when the representative value K therm is out of the reference temperature range, the wearable electronic device 400 may remeasure a value of the at least one first thermistor 410 after a reconfirmation time used for a temperature decrease for each of the temperatures of the internal elements elapses, and may determine whether the remeasured value of the at least one first thermistor 410 is within the reference temperature range.

In operation 730, the wearable electronic device 400 may determine a UI indicating whether the user is in a state in which the body temperature is measurable, when the internal temperature is determined to be within the reference temperature range. If the internal temperature is determined to be within the reference temperature range, the wearable electronic device 400 may estimate a skin temperature trend of the user wearing the wearable electronic device 400, based on a measured value of a second thermistor (e.g., the second thermistor 420 in FIG. 4 and the surface thermistor 625 of FIG. 6C) configured to estimate a user's skin temperature trend outside the wearable electronic device 400. The wearable electronic device 400 may determine the UI, based on at least one of a motion of the user detected by a motion sensor (e.g., the motion sensor 470 of FIG. 4), a variation in a heart rate of the user detected by a PPG sensor (e.g., the PPG sensor 480 of FIG. 4), or a skin temperature trend of the user estimated by the second thermistor 420. A method by which the wearable electronic device 400 determines the UI will be described with reference to FIG. 9.

In operation 740, the wearable electronic device 400 may measure the body temperature by adjusting a body temperature measurement period based on the UI.

The wearable electronic device 400 may acquire the body temperature of the user based on the body temperature measurement period using a temperature sensor (e.g., the temperature sensor 430 of FIG. 4, the non-contact IR temperature sensor 500 of FIG. 5 and the temperature sensor 650 of FIG. 6C) configured to calculate the body temperature of the user based on a temperature change of the internal elements and the skin temperature trend of the user. For example, the wearable electronic device 400 may reduce the body temperature measurement period when the UI is similar to an index indicating the unstable state, and may increase the body temperature measurement period when the UI is similar to an index indicating the stable state. A method by which the wearable electronic device 400 adjusts the body temperature measurement period will be described with reference to FIG. 11 below.

According to an embodiment of the disclosure, the wearable electronic device 400 may correct the body temperature of the user, which is acquired based on the body temperature measurement period, using the measured value of the second thermistor 420 configured to estimate the skin temperature trend of the user outside the wearable electronic device 400.

A method by which the wearable electronic device 400 corrects the body temperature of the user will be described with reference to FIG. 13 below.

Figure 8:
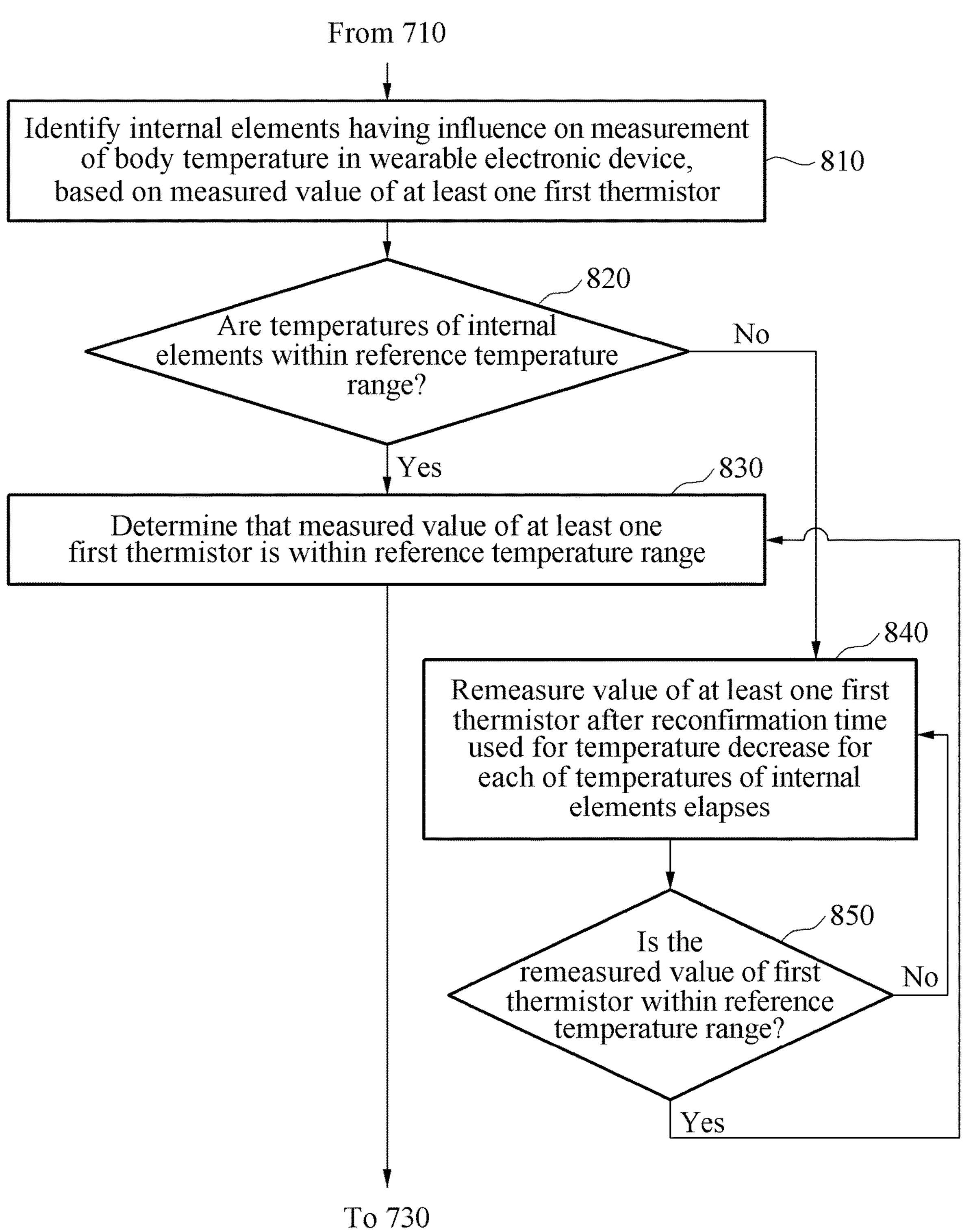
FIG. 8 is a flowchart illustrating a method of determining whether an internal temperature of a wearable electronic device is within a reference temperature range, according to an embodiment of the disclosure.

FIG. 8 is a flowchart illustrating a method of determining whether an internal temperature of a wearable electronic device is within a reference temperature range, according to an embodiment of the disclosure. In the following embodiments of the disclosure, operations may be performed sequentially, but are not necessarily performed sequentially. For example, the order of the operations may be changed and at least two of the operations may be performed in parallel.

Referring to FIG. 8, a wearable electronic device (e.g., the electronic devices 101 and 104 of FIG. 1, the electronic device 200 of FIGS. 2A and 2B, the electronic device 300 of FIG. 3, the wearable electronic device 400 of FIG. 4, and the wearable electronic device 600 of FIG. 6A) according to an embodiment may determine whether the internal temperature of the wearable electronic device 400 is within the reference temperature range through operations 810 to 850.

In operation 810, the wearable electronic device 400 may identify internal elements that have an influence on a measurement of the body temperature in the wearable electronic device 400, based on a measured value of at least one first thermistor (e.g., the at least one first thermistor 410 of FIG. 4, and the battery thermistor 631, the CP thermistor 633, and the AP thermistor 635 of FIG. 6C).

In operation 820, the wearable electronic device 400 may determine whether temperatures of the internal elements are within the reference temperature range (e.g., a range of about 16 to 40° C.). For example, the wearable electronic device 400 may calculate a representative value (e.g., K therm) of the temperatures of the internal elements based on the measured value of the at least one first thermistor 410, and may determine whether the representative value is within the reference temperature range.

If it is determined in operation 820 that the temperatures of the internal elements are within the reference temperature range, the wearable electronic device 400 may determine that the measured value of the at least one first thermistor 410 is within the reference temperature range in operation 830.

Alternatively, if it is determined in operation 820 that the temperatures of the internal elements are out of the reference temperature range, the wearable electronic device 400 may remeasure a value of the at least one first thermistor 410 after a reconfirmation time used for a temperature decrease for each of the temperatures of the internal elements elapses in operation 840. If the temperatures of the internal elements are out of the reference temperature range, the wearable electronic device 400 may set the reconfirmation time by checking temperatures of internal elements that generate heat, and may remeasure the temperatures of the internal elements that generate heat after the reconfirmation time elapses. A method by which the wearable electronic device 400 sets the reconfirmation time is described below.

The wearable electronic device 400 may identify a heat generation portion by determining a measured value of each of the at least one first thermistor 410, and may optimize a remeasurement time for analyzing a heat generation state based on a heat generation level of the heat generation portion.

Reconfirmation times used for a temperature decrease for each of temperatures of internal elements may be set, for example, as shown in Table 1 below.

TABLE 1

| Variation in temperature of heat generation portion (Temperature of thermistor-40° C.) | Reconfirmation time |
|---|---|
| 0-5° C. | 60 sec |
| 5-10° C. | 180 sec |
| 10-20° C. | 300 sec |
| 20° C. or greater | 600 sec |

TABLE 1-continued

| Variation in temperature of heat generation portion (Temperature of thermistor-40° C.) | Reconfirmation time |
|---|---|

In an example in which 40° C. is set as a reference temperature, when the internal temperature by the internal elements is greater than 40° C. by about 0 to 5° C., a relatively small amount of time (e.g., 60 seconds (sec)) may be used to reduce a temperature of an internal element to 40° C. or less. In this example, when the internal temperature is greater than 40° C. by 20° C. or greater, a relatively large amount of time (e.g., 600 sec) may be used to reduce a temperature of an internal element to a stable temperature below 40° C.

If heat with a temperature exceeding 40° C. is generated in the internal elements, the wearable electronic device 400 may measure a temperature again using the at least one first thermistor 410 at a point in time at which the heat is dissipated, to determine whether a user's body temperature is measurable, that is, whether the internal temperature does not have an influence on the measurement of the body temperature. To this end, the wearable electronic device 400 may adjust the reconfirmation time to remeasure the temperature of the at least one first thermistor 410 for each temperature difference as shown in Table 1.

In operation 850, the wearable electronic device 400 may determine whether the value of the at least one first thermistor 410 remeasured in operation 840 is within the reference temperature range. In an example, if it is determined in operation 850 that the remeasured value of the at least one first thermistor 410 is within the reference temperature range, the wearable electronic device 400 may determine that the measured value of the at least one first thermistor 410 is within the reference temperature range in operation 830. In another example, if it is determined in operation 850 that the remeasured value of the at least one first thermistor 410 is out of the reference temperature range, the value of the at least one first thermistor 410 may be remeasured in operation 840.

Figure 9:
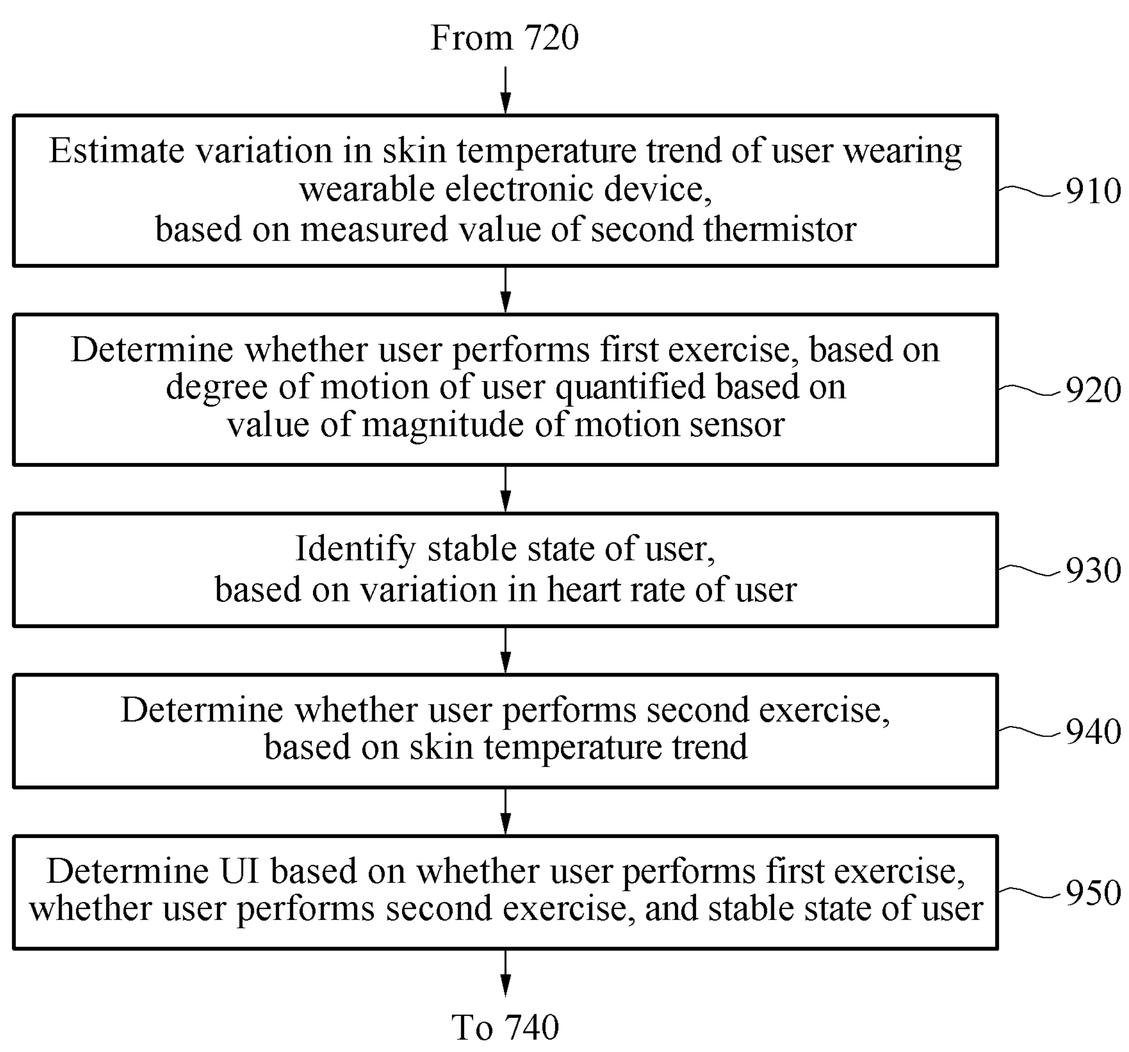
FIG. 9 is a flowchart illustrating a method of determining a user state index according to an embodiment of the disclosure.

FIG. 9 is a flowchart illustrating a method of determining a UI according to an embodiment of the disclosure. In the following embodiments of the disclosure, operations may be performed sequentially, but are not necessarily performed sequentially. For example, the order of the operations may be changed and at least two of the operations may be performed in parallel.

Referring to FIG. 9, a wearable electronic device (e.g., the electronic devices 101 and 104 of FIG. 1, the electronic device 200 of FIGS. 2A and 2B, the electronic device 300 of FIG. 3, the wearable electronic device 400 of FIG. 4, and the wearable electronic device 600 of FIG. 6A) according to an embodiment may determine the UI through operations 910 to 950.

The fundamental reason for measuring a body temperature is to detect diseases, such as colds, body aches, and infectious diseases. However, when an exercise is performed or when the weather is hot, the wearable electronic device 400 for measuring a body temperature may incorrectly determine a body temperature increased due to the exercise and/or a surrounding environment, such as the weather to be a fever of a person. Therefore, the wearable electronic device 400 may separate a normal body temperature measurement and a body temperature increased due to the exercise and/or surrounding environment, to more accurately measure a body temperature.

In operation 910, the wearable electronic device 400 may estimate a variation (e.g., ΔSkin temperature trend) in a skin temperature trend of a user wearing the wearable electronic device 400, based on a measured value of a second thermistor (e.g., the second thermistor 420 of FIG. 4 and the surface thermistor 625 of FIG. 6C). A method by which the wearable electronic device 400 estimates the skin temperature trend of the user will be described with reference to FIG. 10 below.

In operation 920, the wearable electronic device 400 may determine whether the user performs a first exercise, using a function of a duration and a degree (e.g., ΔACC) of motion of the user quantified based on a value of a magnitude of a motion sensor (e.g., the motion sensor 470 of FIG. 4). In an example, when a state in which the degree (e.g., ΔACC) of motion of the user is "0" is determined to last for 2 seconds or greater, the wearable electronic device 400 may determine that the user is not moving, that is, the user is not exercising. In another example, when a state in which the degree (e.g., ΔACC) of motion of the user is "1" is determined to last for 2 seconds or greater, the wearable electronic device 400 may determine that the user is moving, that is, the user is exercising.

Although the wearable electronic device 400 may determine whether the user is moving based on an index value (e.g., "0" or "1") indicating the degree (e.g., ΔACC) of motion of the user, and may also define a state of motion of the user variously based on an output value of a motion sensor (e.g., the motion sensor 470 of FIG. 4), such as an acceleration sensor.

The wearable electronic device 400 may quantify a state of the user based on a value of a magnitude of the motion sensor 470. In an example, if a user's motion corresponds to a simple motion that may not be regarded as an exercise even if the user is moving, the wearable electronic device 400 may determine a state of the user to be a sedentary state in which there is no motion. In another example, if a user's motion corresponds to a repetitive pattern or an impact with a large motion, the wearable electronic device 400 may determine a state of the user to be an exercise state, such as a state of performing a predetermined exercise. When the state of the user is determined to be the exercise state, the wearable electronic device 400 may limit a measurement of the body temperature or notify that a measured body temperature is a body temperature measured during exercise, because heat generated due to the exercise may have an influence on the measurement of the body temperature.

In operation 930, the wearable electronic device 400 may identify a stable state of the user, based on whether a variation (e.g., APPG) in a heart rate of the user lasts for a reference time or greater. The variation in the heart rate may correspond to a difference between a heart rate of the user measured by a PPG sensor (e.g., the PPG sensor 480 of FIG. 4) and a resting heart rate of the user. The wearable electronic device 400 may identify the stable state of the user, based on whether the variation (e.g., APPG) corresponding to the difference between the heart rate of the user by a value of a heart rate measured by the PPG sensor 480 and a pre-stored resting heart rate of the user lasts for the reference time or greater.

Since a heart rate varies according to a person's age, gender, and health condition, a stable heart rate state may be personalized for each individual. For example, if a large amount of exercise is performed, the overall heart rate may drop, and if the age increases, a heart rate may drop.

Therefore, a degree of stabilization of a heart rate may be determined by the variation (e.g., APPG) corresponding to the difference between the measured heart rate and the resting heart rate.

In an example, when a value of a state flag is set to "0" due to the variation (e.g., APPG) lasting for less than the reference time, the wearable electronic device 400 may determine the heart rate of the user to be in a stable state (e.g., a range of about 61 to 80 beats per minute (bpm)). In another example, when the value of the status flag is set to "1" due to the variation (e.g., APPG) lasting for the reference time or greater, the wearable electronic device 400 may determine the heart rate to be in an unstable state (e.g., out of a range of about 61 to 80 bpm).

In operation 940, the wearable electronic device 400 may determine whether the user performs a second exercise, based on the variation (e.g., ΔSkin temperature trend) in the skin temperature trend estimated in operation 910.

If the user performs an exercise, a variation in a skin temperature may increase. In general, a skin temperature may be used to identify whether a user moves relatively accurately in comparison to a PPG signal. However, the skin temperature may be inaccurate in some circumstances due to an error due to sweat and an influence of an external temperature. According to an embodiment of the disclosure, an accuracy of estimation of a user state may be enhanced using the PPG signal and the skin temperature trend together.

In operation 950, the wearable electronic device 400 may determine the UI, based on whether the user performs the first exercise determined in operation 920, whether the user performs the second exercise determined in operation 940, and the stable state of the user identified in operation 930.

For example, the wearable electronic device 400 may determine a user index Ui, as shown in Equation 2 below.

$$Ui(\text{user index}) = \Delta ACC + \Delta PPG + \Delta\text{Skin temperature trend} \quad \text{Equation 2}$$

The user index Ui may be determined by, for example, a degree ΔACC of motion of a user, a variation ΔPPG in a heart rate of the user, and a variation ΔSkin temperature trend in a skin temperature trend of the user.

In an embodiment of the disclosure, the user index Ui may correspond to a value used to determine whether a user is in a state suitable to measure a body temperature. Here, each item (e.g., dACC, dPPG, and dSkin) used to determine the user index Ui may have a value of "1" corresponding to TRUE or a value of "0" corresponding to FALSE. For example, the user index Ui of "3" may correspond to an unstable state that is a state most unsuitable for a user to measure a body temperature. In addition, the user index Ui of "0" may correspond to a stable state that is a state most suitable for a user to measure a body temperature.

According to an embodiment of the disclosure, the wearable electronic device 400 may also determine the user index Ui using any one or any combination of the above-described items. For example, the wearable electronic device 400 may determine the user index Ui, using a skin temperature trend dSkin and a user motion dACC, using the skin temperature trend dSkin and a heart rate variation dPPG, or using the user motion dACC and the heart rate variation dPPG. In an embodiment of the disclosure, user state variables used to determine the user index Ui may be variously combined. At least one of the above-described user state variables may be used to determine the user index Ui, and an additional user state variable, such as a variable indicating whether the user performs the second exercise by the skin temperature trend, may be further used. The wearable electronic device 400 may more precisely determine the state of the user, in response to an increase in a number of user state variables used to determine the user index Ui.

According to an embodiment of the disclosure, the wearable electronic device 400 may assign different weights for each of user state variables used to determine the user index Ui. For example, the wearable electronic device 400 may assign different weights for each of the user state variables based on a surrounding environment or the user and/or a mental state of the user, and may also determine the user state Ui.

Figure 10:
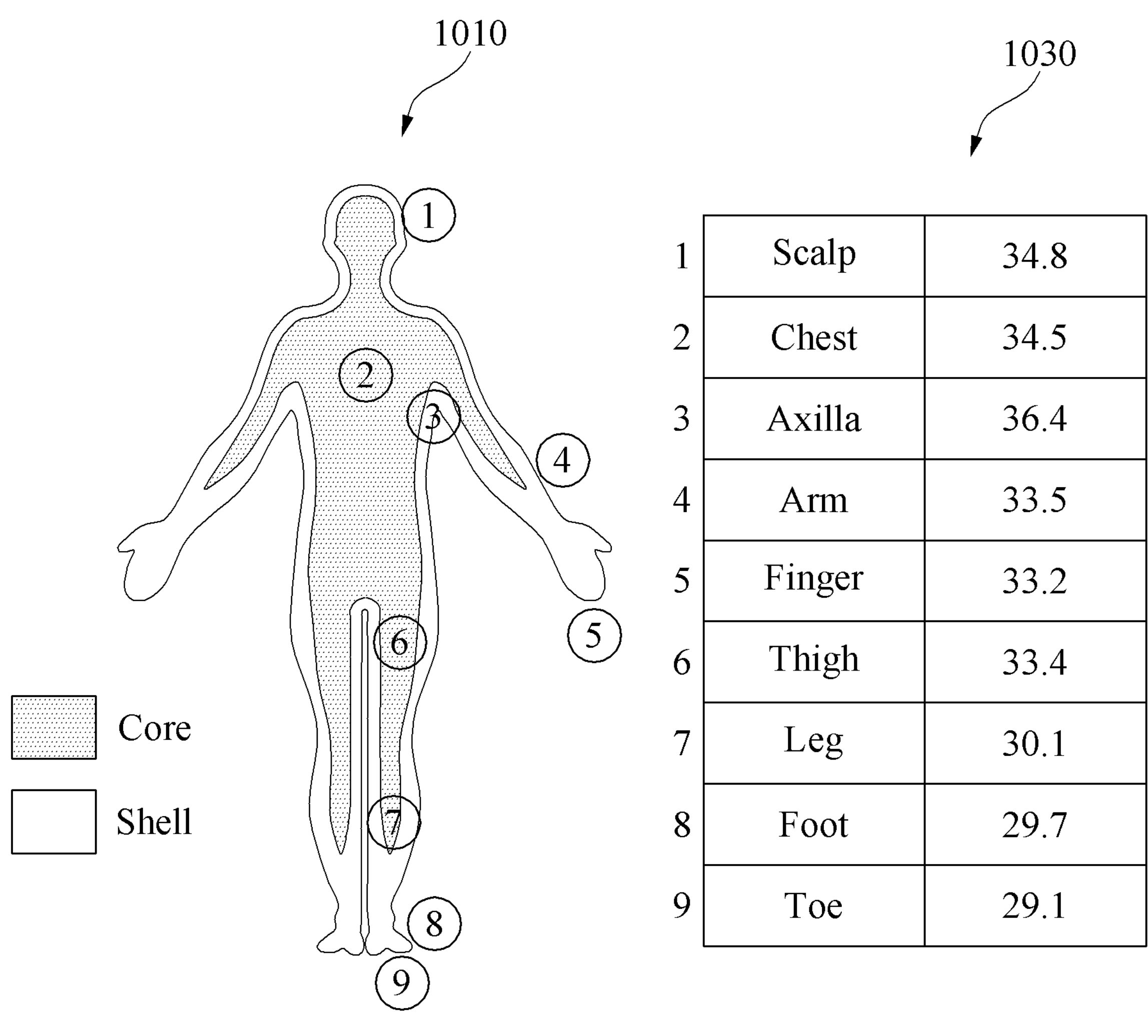
FIG. 10 is a diagram illustrating a method of estimating a skin temperature trend according to an embodiment of the disclosure.

FIG. 10 is a diagram illustrating a method of estimating a skin temperature trend of a user according to an embodiment of the disclosure. Referring to FIG. 10, a table 1030 shows a body temperature distribution by body parts of a person 1010 (e.g., ① scalp, ② chest, ③ axilla, ④ arm, ⑤ finger, ⑥ thigh, ⑦ leg, ⑧ foot, (⑨ toe) at a predetermined temperature according to an embodiment of the disclosure.

A wearable electronic device (e.g., the electronic devices 101 and 104 of FIG. 1, the electronic device 200 of FIGS. 2A and 2B, the electronic device 300 of FIG. 3, the wearable electronic device 400 of FIG. 4, and the wearable electronic device 600 of FIG. 6A) may estimate a skin temperature trend of a user, using a second thermistor (e.g., the second thermistor 420 of FIG. 4 and the surface thermistor 625 of FIG. 6C) to determine whether the user is in a state in which body temperature measurement is possible. As the second thermistor 420, the above-described surface thermistor may be used. The surface thermistor may belong to the second thermistor 420, and may also belong to a first thermistor (e.g., the at least one first thermistor 410 in FIG. 4, and the battery thermistor 631, the CP thermistor 633, and the AP thermistor 635 of FIG. 6C). In an embodiment of the disclosure, the at least one first thermistor 410 and the second thermistor 420 may be physically distinguished from each other, but may also be functionally distinguished abstract categorizations.

For example, heat generated in the wearable electronic device 400 and heat detected from a user may have an influence on a temperature sensor (e.g., the temperature sensor 430 of FIG. 4, the non-contact IR temperature sensor 500 of FIG. 5, and the temperature sensor 650 of FIG. 6C). According to an embodiment of the disclosure, a user's body temperature to be measured may be largely divided into a body temperature, a skin temperature, and a core temperature. The body temperature may correspond to a representative temperature to estimate a health state of a body of the person 1010. The body temperature may be used worldwide in common, and may be set based on a location in which a state may be estimated when a fever occurs, for example, in an axilla, a forehead, the inside of an ear, or in an oral cavity. As described above, the skin temperature may correspond to a temperature corresponding to a skin part in contact with a temperature sensor (e.g., the second thermistor 420). The core temperature may correspond to, for example, a temperature of an internal organ of a body, such as a heart or a bladder, and may be distinguished from a shell temperature, such as a skin or a distal part of a body, such as a finger and toe.

However, a temperature measured by the wearable electronic device 400 may be, for example, a temperature of a wrist, a finger, or an external ear, and may correspond to a skin temperature. In other words, a measurement point of the wearable electronic device 400 may be different from that of a thermometer. The wearable electronic device 400 may correct a measured skin temperature value to a body temperature value so that skin temperatures measured at different measurement points may be standardized to a body temperature. The wearable electronic device 400 may standardize a skin temperature X measured by the second thermistor 420 at a measurement point to a body temperature value by reflecting a compensation coefficient k' to the skin temperature X as in X*k'. The compensation coefficient k' may correspond to a coefficient for compensating for a skin temperature to a body temperature. As described above, the skin temperature standardized to the body temperature value may correspond to a skin temperature trend.

Figure 11:
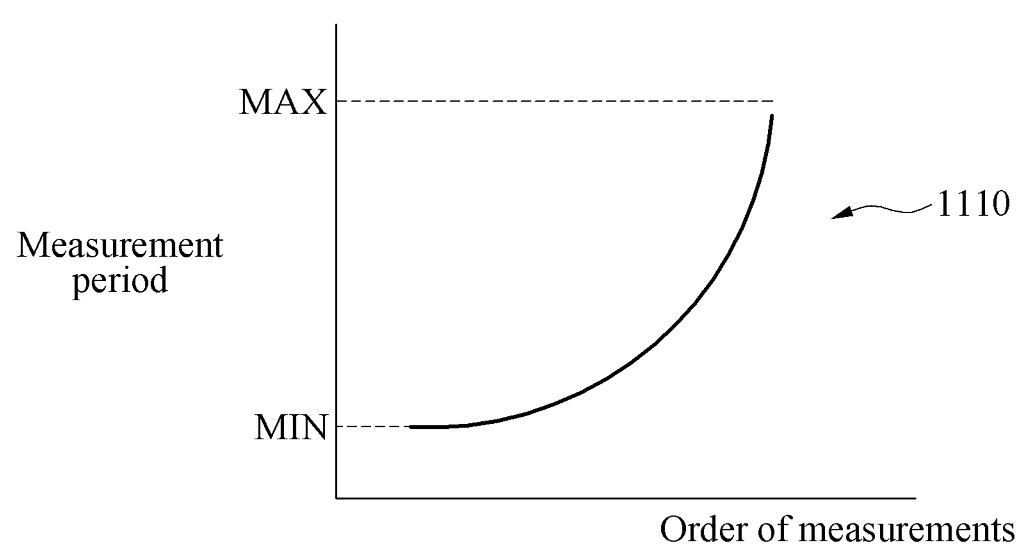
FIG. 11 is a diagram illustrating a method of controlling a body temperature measurement period based on a user state index, according to an embodiment of the disclosure.

FIG. 11 is a diagram illustrating a method of controlling a body temperature measurement period based on a UI according to an embodiment of the disclosure.

Referring to FIG. 11, a graph 1110 shows a relationship between a body temperature measurement period and an order of measurements, and a table 1130 shows a measurement period and a state of a user corresponding to a UI, according to an embodiment of the disclosure.

A wearable electronic device (e.g., the electronic devices 101 and 104 of FIG. 1, the electronic device 200 of FIGS. 2A and 2B, the electronic device 300 of FIG. 3, the wearable electronic device 400 of FIG. 4, and the wearable electronic device 600 of FIG. 6A) according to an embodiment may measure a body temperature of a user by adjusting a body temperature measurement period using a temperature sensor (e.g., the temperature sensor 430 of FIG. 4, the non-contact IR temperature sensor 500 of FIG. 5, and the temperature sensor 650 of FIG. 6C). The wearable electronic device 400 may determine a body temperature measurement period of a next user, based on the UI.

For example, a measurement period for measuring a user's body temperature may increase in proportion to an increase in a number N of times of measurements, as shown in the graph 1110. The measurement period may have various values from a minimum value (e.g., 5 minutes (min)) to a maximum value (e.g., 60 min).

The wearable electronic device 400 may adjust a next measurement period according to a user's state, for example, as shown in the table 1130.

Since a body temperature does not significantly change in comparison to a heart rate and lasts for a relatively long period of time when a user has a fever, a measurement period may be short in comparison to the heart rate. For example, when a user is in a stable state, the wearable electronic device 400 may measure a body temperature once every 60 minutes. Since a relatively small number of factors have an influence on a measurement of a body temperature in the stable state, a value may be accurately measured even though a body temperature is measured once every 60 minutes.

In another example, when a user is exercising or a motion of the user is large, a state of the user may be unstable. If the user is in the unstable state, the wearable electronic device 400 may reduce a measurement period to closely respond to a biometric change. If the user is in the unstable state, the wearable electronic device 400 may more closely and accurately analyze the user's state by shortening the measurement period. If the unstable state is maintained, the wearable electronic device 400 may more accurately and quickly collect information on a state of a change in the body temperature by continuing to measure body temperatures in a relatively short measurement period for 24 hours.

For example, a measurement period for a first measurement may be assumed to be set to 5 min which is the minimum value. In this example, if the UI is determined to be "0" corresponding to the stable state, the wearable electronic device 400 may gradually increase the measurement period from 5 min to 10 min, 30 min, and 60 min. In another example, if the UI is determined to be "2" corresponding to the unstable state when the measurement period is set to 30 min, the wearable electronic device 400 may reduce the measurement period from 30 min to 10 min.

The wearable electronic device 400 may adjust the body temperature measurement period according to the UI, for example, as shown in Table 1130, and may increase the body temperature measurement period when the user is in the stable state, thereby reducing an amount of current to be consumed to measure a body temperature. When the user is in the unstable state, the wearable electronic device 400 may reduce the body temperature measurement period, thereby increasing an accuracy of measurement of a body temperature.

Figure 12:
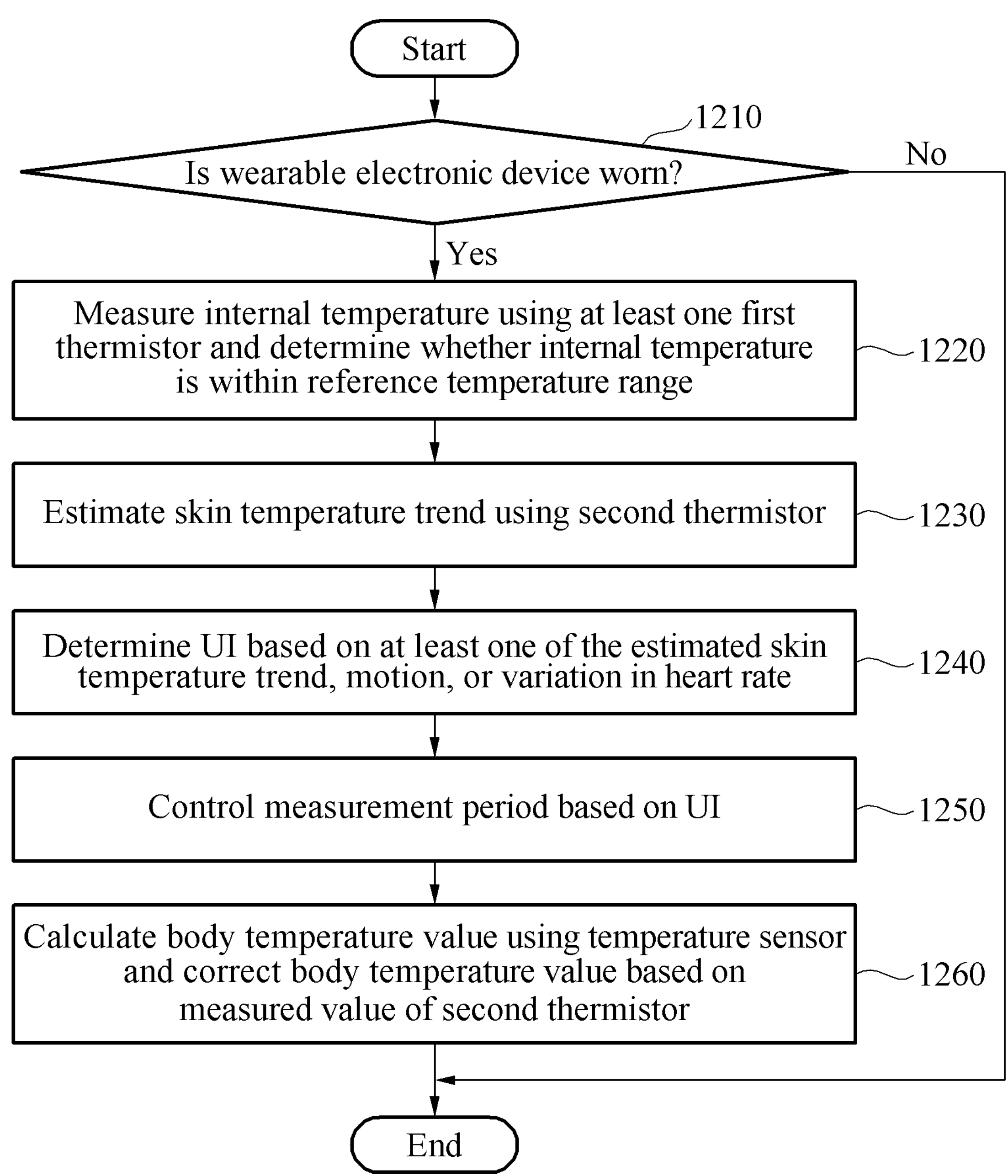
FIG. 12 is a flowchart illustrating a method of operating a wearable electronic device according to an embodiment of the disclosure.

FIG. 12 is a flowchart illustrating a method of operating a wearable electronic device according to an embodiment of the disclosure. In the following embodiments of the disclosure, operations may be performed sequentially, but are not necessarily performed sequentially. For example, the order of the operations may be changed and at least two of the operations may be performed in parallel.

Referring to FIG. 12, a wearable electronic device (e.g., the electronic devices 101 and 104 of FIG. 1, the electronic device 200 of FIGS. 2A and 2B, the electronic device 300 of FIG. 3, the wearable electronic device 400 of FIG. 4, and the wearable electronic device 600 of FIG. 6A) according to an embodiment may correct a body temperature value measured using a temperature sensor (e.g., the temperature sensor 430 of FIG. 4, the non-contact IR temperature sensor 500 of FIG. 5, and the temperature sensor 650 of FIG. 6C) based on a measurement period, through operations 1210 to 1260.

In operation 1210, the wearable electronic device 400 may determine whether the wearable electronic device 400 is worn. The wearable electronic device 400 may determine whether a user wears the wearable electronic device 400 by a contact sensor (e.g., the contact sensor 490 of FIG. 4). If it is determined in operation 1210 that the user does not wear the wearable electronic device 400 (No), the wearable electronic device 400 may terminate an operation or may wait until whether the wearable electronic device 400 is worn is detected by the contact sensor 490.

In an example, it may be assumed that the user is determined to wear the wearable electronic device 400 (Yes) in operation 1210. In this example, in operation 1220, the wearable electronic device 400 may measure an internal temperature of the wearable electronic device 400 using at least one first thermistor (e.g., the at least one first thermistor 410 of FIG. 4, and the battery thermistor 631, the CP thermistor 633, and the AP thermistor 635 of FIG. 6C) and determine whether the internal temperature is within a reference temperature range. When it is determined in operation 1220 that the internal temperature of the wearable electronic device 400 is out of the reference temperature range, the wearable electronic device 400 may wait until it is determined that the internal temperature is within the reference temperature range.

In another example, it may be assumed that the internal temperature of the wearable electronic device 400 is determined to be within the reference temperature range in operation 1220. In this example, in operation 1230, the wearable electronic device 400 may estimate a skin temperature trend using a second thermistor (e.g., the second thermistor 420 of FIG. 4 and the surface thermistor 625 of FIG. 6C). The wearable electronic device 400 may estimate the skin temperature trend by, for example, the method described above with reference to FIG. 10.

In operation 1240, the wearable electronic device 400 may determine a UI, based on at least one of the skin temperature trend (e.g., dSkin) estimated in operation 1230, a motion (e.g., dACC) of the user detected by a motion sensor (e.g., the motion sensor 470 of FIG. 4), or a variation (e.g., dPPG) in a heart rate of the user detected by a PPG sensor (e.g., the PPG sensor 480 of FIG. 4).

In operation 1250, the wearable electronic device 400 may control or adjust a measurement period based on the UI determined in operation 1240.

In operation 1260, the wearable electronic device 400 may measure a body temperature value using the temperature sensor 430 based on the measurement period controlled in operation 1250, and may correct the body temperature value measured by the temperature sensor 430, based on a measured value of the second thermistor 420.

Figure 13:
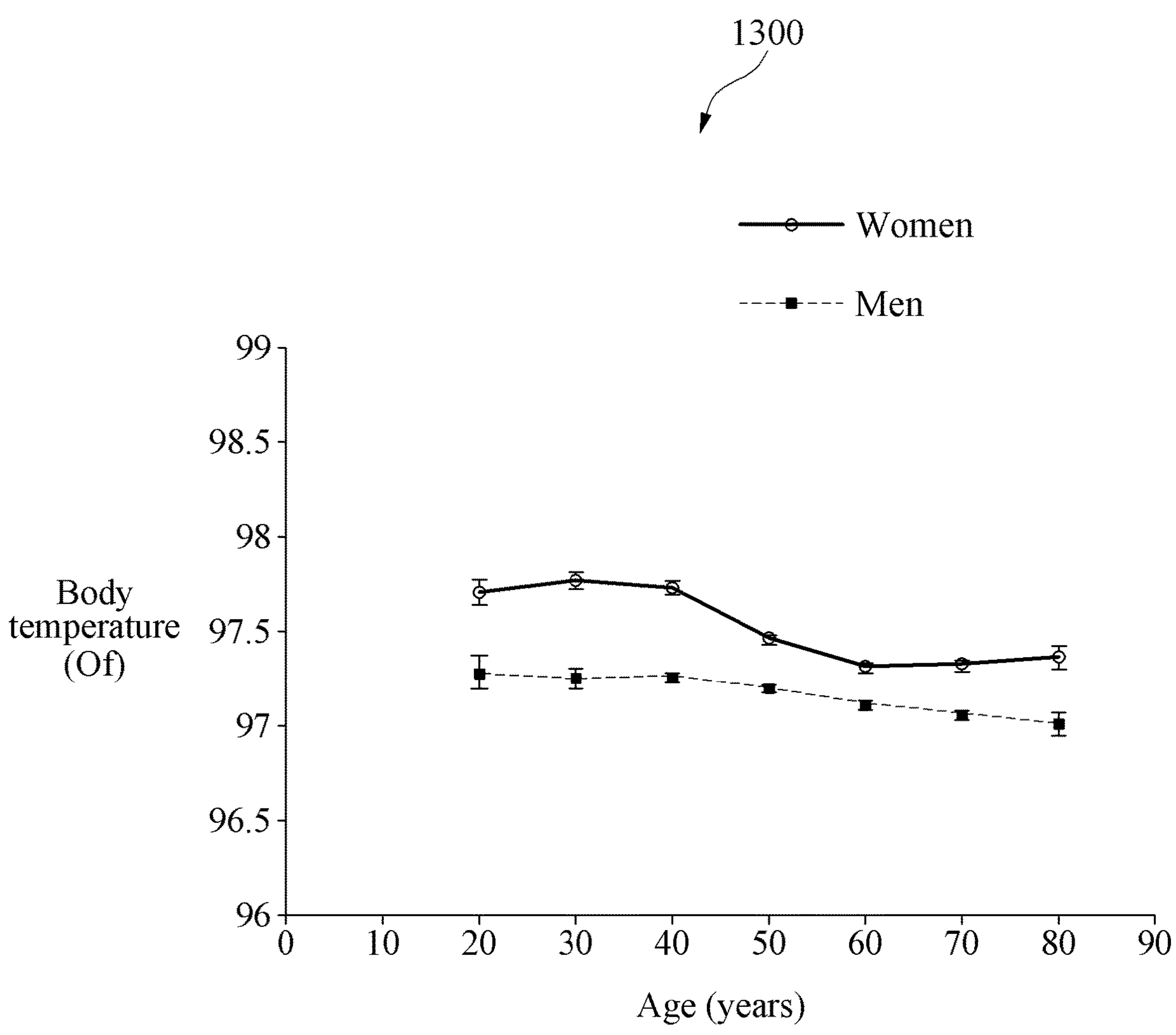
FIG. 13 is a diagram illustrating a method of correcting a body temperature of a user according to an embodiment of the disclosure.

FIG. 13 is a diagram illustrating a method of correcting a body temperature of a user according to an embodiment of the disclosure.

Referring to FIG. 13, a graph 1300 shows a change in a body temperature according to age/gender according to an embodiment of the disclosure.

A wearable electronic device (e.g., the electronic devices 101 and 104 of FIG. 1, the electronic device 200 of FIGS. 2A and 2B, the electronic device 300 of FIG. 3, the wearable electronic device 400 of FIG. 4, and the wearable electronic device 600 of FIG. 6A) according to an embodiment may calculate a body temperature using a temperature sensor (e.g., the temperature sensor 430 of FIG. 4, the non-contact IR temperature sensor 500 of FIG. 5, and the temperature sensor 650 of FIG. 6C) based on the measurement period adjusted through the above-described process.

A normal body temperature measurement range for each individual may be determined based on, for example, age, gender, and/or a measurement location. A normal body temperature may be generally within a range of about 35.9° C. to 37.6° C. A normal body temperature for an ear may be in a range of about 35.8° C. to 37.8° C., a normal body temperature for a mouth may be in a range of about 35.5° C. to 37.5° C., a normal body temperature for an axilla may be in a range of about 35.3° C. to 37.3° C., and a normal body temperature for an anus may be in a range of about 36.6° C. to 37.9° C. In addition, a normal body temperature for infants under 3 months of age may be in a range of about 35.8° C. to 37.4° C., a normal body temperature for infants from 3 months to 36 months may be in a range of about 35.4° C. to 37.6° C., and a normal body temperature for infants over 36 months may be in a range of about 35.4° C. to 37.7° C.

For example, the wearable electronic device 400 may prepare a table including body temperature values corresponding to measured values (e.g., a skin temperature) of a second thermistor (e.g., the second thermistor 420 of FIG. 4, and the surface thermistor 625 of FIG. 6C) according to age, gender, and/or measurement locations in advance, and may correct a body temperature calculated by the temperature sensor 430 based on the table.

Since the wearable electronic device 400 is aware of information about a user, such as the age and gender of the user, in advance, a matching value of a skin temperature may not be simply unified. For example, the wearable electronic device 400 may divide users into male and female, adolescents/adults/old people, and may correct the calculated body temperature by individually applying a correction value that is based on the user information to a measured sensor value. For example, the wearable electronic device 400 may apply a skin temperature correction value of an adolescent male and a skin temperature correction value of an elderly woman differently.

Figure 14:
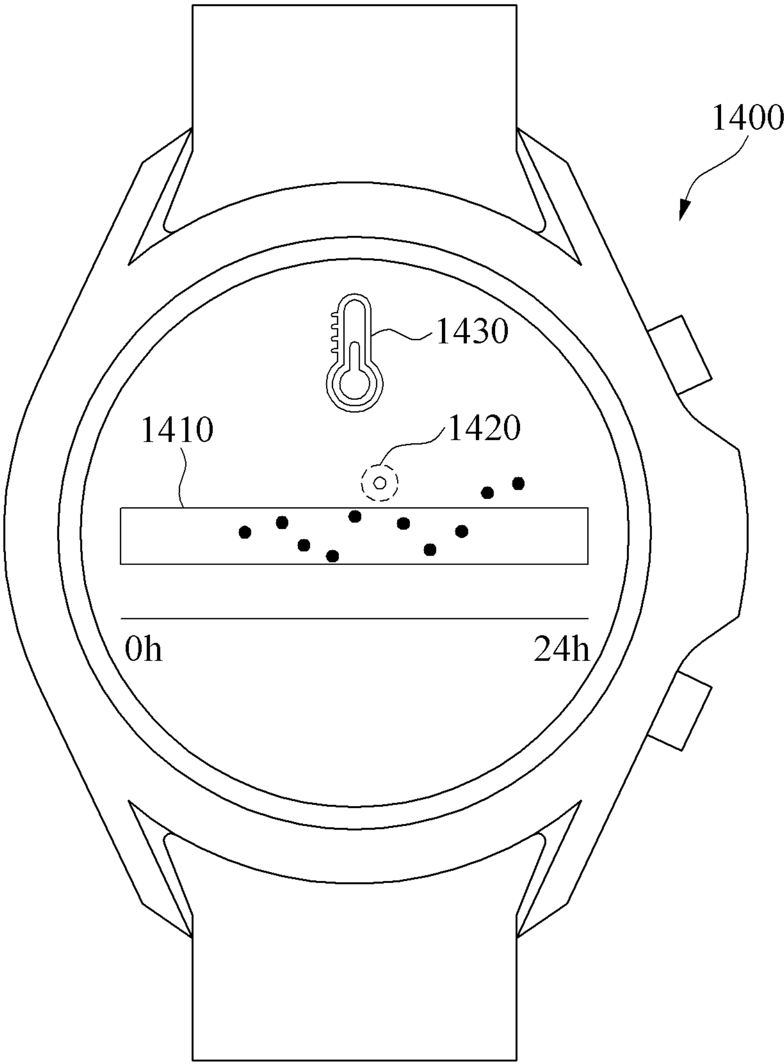
FIG. 14 is a diagram illustrating a wearable electronic device displays a measured body temperature value according to an embodiment of the disclosure.

FIG. 14 is a diagram illustrating a wearable electronic device displays measured body temperature values according to an embodiment of the disclosure.

Referring to FIG. 14, a wearable electronic device (e.g., the electronic devices 101 and 104 of FIG. 1, the electronic device 200 of FIGS. 2A and 2B, the electronic device 300 of FIG. 3, the wearable electronic device 400 of FIG. 4, and the wearable electronic device 600 of FIG. 6A) according to an embodiment may display measured body temperature values on a screen 1400.

The wearable electronic device 400 may monitor a body temperature of a user for 24 hours. The wearable electronic device 400 may display measured body temperature values in the form of a graph as shown on the screen 1400.

For example, as shown on the screen 1400, the wearable electronic device 400 may set a reference temperature range 1410 that may be determined as a normal body temperature based on user's personal characteristics (e.g., gender, age, a measurement range, and pre-measured information), and may display a body temperature included in the reference temperature range 1410 as a normal body temperature.

However, a measured body temperature may deviate from the reference temperature range 1410 corresponding to a normal state. An example in which the measured body temperature is out of the reference temperature range 1410 may include, for example, an example in which a user has a fever and an example in which heat is generated due to other factors (e.g., heat temporarily generated due to hot weather or exercise, such as running).

The wearable electronic device 400 may distinguish the example in which the user has a fever from the example in which the heat is generated due to the other factors and may display the above examples, based on a result obtained by detecting a user's motion using a motion sensor (e.g., the motion sensor 470 of FIG. 4), such as an acceleration sensor or a gyro sensor.

For example, when the user actually has a fever, the wearable electronic device 400 may display a point in time at which a body temperature is measured based on a measurement period of a temperature sensor, and a body temperature value measured at the point in time, and may display or transmit an alarm indicating that the user is in a fever state. When the fever state of the user lasts, the wearable electronic device 400 may suggest that the user go to a hospital, inform the user of measures according to the fever, or remotely connect the user with a doctor. When the fever state of the user lasts, the wearable electronic device 400 may frequently measure the body temperature by adjusting the measurement period to be short, for example, at an interval of ten minutes, and may maintain a relatively short measurement period until the user's body temperature is restored to the normal temperature.

For example, the wearable electronic device 400 may periodically measure and display the body temperature. For example, when a user's body temperature is periodically measured, if it is determined that a user's state is not a state suitable to measure the body temperature, the wearable electronic device 400 may skip a body temperature measurement and may not display the body temperature. Here, a case in which it is determined that the user's state is not a state suitable to measure the body temperature may include, for example, a case in which a user's motion is large, a heart rate is high, heat is generated due to exercise, and/or a temperature is high. In this example, the wearable electronic device 400 may reduce a measurement period until it is suitable to measure the body temperature, and may remeasure the body temperature after "n" minutes. Here, "n" may be a constant greater than "0". The wearable electronic device 400 may periodically measure and display a body temperature. If it is suspected that a body temperature measurement result is not accurate, the wearable electronic device 400 may display the suspected measurement result differently from a general body temperature.

For example, if heat is generated due to other factors, the wearable electronic device 400 may exclude the generated heat from a measurement. In this example, the wearable electronic device 400 may differently display a body temperature measured at a corresponding point in time as indicated by reference numeral 1420 (e.g., an empty circle) to inform that the heat is generated due to the other factors, or may display a thermometer icon 1430 indicating a reason (e.g., a high temperature) corresponding to the generated heat together with the body temperature.

For example, when the user's state becomes suitable to measure the body temperature, the wearable electronic device 400 may also measure the user's body temperature. If there is no user's motion, if "n1" hours have elapsed since the body temperature was measured, and if other conditions (e.g., a variation in a user's heart rate, and/or a variation in a user's skin temperature trend which are other factors to determine a user index Ui) indicating the user's state are satisfied, the wearable electronic device 400 may measure the user's body temperature. When conditions indicating the user's state fail to satisfy a state suitable to measure the user's body temperature, the wearable electronic device 400 may remeasure the user's body temperature at a measurement time of "n2" (n1>n2).

In addition, the wearable electronic device 400 may measure and display a body temperature periodically or according to circumstances. The wearable electronic device 400 may correct a body temperature value measured using, for example, the motion sensor 470, a PPG sensor (e.g., the PPG sensor 480 of FIG. 4), and/or a thermistor (e.g., the at least one first thermistor 410 and the second thermistor 420 of FIG. 4) and display the body temperature value. If the body temperature value is corrected and displayed, the wearable electronic device 400 may display an error rate (e.g., ±several degrees) together.

According to an embodiment of the disclosure, the wearable electronic device 400 may determine a measurement situation through machine learning and may measure a user's body temperature adaptively, that is, irregularly. The wearable electronic device 400 may monitor a user's situation and also correct a measured body temperature value through machine learning.

According to an embodiment of the disclosure, a wearable electronic device may automatically continue to measure a user's body temperature using a non-contact IR body temperature sensor.

According to an embodiment of the disclosure, a wearable electronic device may detect a change in temperatures of internal elements, and may remeasure an internal temperature after a predetermined period of time when the internal temperature has an influence on a calculation of a user's body temperature, to reduce an influence of the temperatures of the internal elements during a measurement of a body temperature.

According to an embodiment of the disclosure, a wearable electronic device may determine a UI indicating whether a user is in a state in which a body temperature is measurable, and may measure the body temperature when the user is in the state in which the body temperature is measurable based on the UI, to increase an accuracy of a measurement of the body temperature.

According to an embodiment of the disclosure, a wearable electronic device may adjust a body temperature measurement period according to the UI. Accordingly, when a user is in a stable state, the wearable electronic device may increase the body temperature measurement period, to reduce an amount of current to be consumed for a body temperature measurement. When the user is in an unstable state, the wearable electronic device may reduce the body temperature measurement period, to increase an accuracy of a measurement of the body temperature.

According to an embodiment of the disclosure, a wearable electronic device may quickly measure an accurate point in time at which heat is generated and a body temperature corresponding to the point in time, for a situation in which heat is irregularly generated by a user, to allow an immediate action to be performed.

According to an embodiment of the disclosure, a wearable electronic device 101, 104, 200, 300, 400, 600 may include at least one first thermistor 410, 631, 633, 635 arranged in different heat generation positions in the wearable electronic device 101, 104, 200, 300, 400, 600 and configured to detect a temperature change of internal elements 602, 604, 605 of the wearable electronic device 101, 104, 200, 300, 400, 600, a temperature sensor 430, 500, 650 configured to calculate a body temperature of a user based on the temperature change of the internal elements 602, 604, 605 and a skin temperature trend of the user, and a processor 120, 440 configured to determine whether an internal temperature by the internal elements 602, 604, 605 in the wearable electronic device 101, 104, 200, 300, 400, 600 is within a reference temperature range that does not have an influence on a calculation of the body temperature, based on a measured value of the at least one first thermistor 410, 631, 633, 635, configured to determine a UI indicating whether the user is in a state in which the body temperature is measurable, when the internal temperature is determined to be within the reference temperature range, and configured to measure the body temperature by adjusting a body temperature measurement period based on the UI.

According to an embodiment of the disclosure, the wearable electronic device 101, 104, 200, 300, 400, 600 may further include a contact sensor 490 configured to detect whether the user is in contact with the wearable electronic device. The processor 120, 440 may be configured to determine whether the internal temperature is within the reference temperature range based on the measured value of the at least one first thermistor 410, 631, 633, 635, when it is determined by the contact sensor 490 that the user wears the wearable electronic device 101, 104, 200, 300, 400, 600.

According to an embodiment of the disclosure, the internal elements 602, 604, 605 may include at least one of an AP 120, 605, a battery 189, 602, or a CP 120, 440.

According to an embodiment of the disclosure, the processor 120, 440 may be configured to calculate a representative value of temperatures of the internal elements 602, 604, 605 based on the measured value of the at least one first thermistor 410, 631, 633, 635, and determine whether the representative value is within the reference temperature range.

According to an embodiment of the disclosure, the processor 120, 440 may be configured to assign different weights for each measured value of the at least one first thermistor 410, 631, 633, 635 and calculate the representative value.

According to an embodiment of the disclosure, the processor 120, 440 may be configured to remeasure a value of the at least one first thermistor 410, 631, 633, 635 after a reconfirmation time used for a temperature decrease for each of the temperatures of the internal elements 602, 604, 605 elapses, when the representative value is determined to be out of the reference temperature range, and determine whether the remeasured value of the first thermistor is within the reference temperature range.

According to an embodiment of the disclosure, the wearable electronic device 101, 104, 200, 300, 400, 600 may further include at least one of a motion sensor 470 configured to detect a motion of the user, a PPG sensor 480 configured to detect a heart rate of the user, or a second thermistor 420, 625 configured to estimate the skin temperature trend of the user outside the wearable electronic device 101, 104, 200, 300, 400, 600. The processor 120, 440 may be configured to estimate the skin temperature trend of the user wearing the wearable electronic device 101, 104, 200, 300, 400, 600 using a measured value of the second thermistor 420, 625, when the internal temperature is determined to be within the reference temperature range, and determine the UI based on at least one of the motion of the user, a variation in the heart rate of the user, or the skin temperature trend of the user.

According to an embodiment of the disclosure, the processor 120, 440 may be configured to determine whether the user performs a first exercise, based on a degree of motion of the user quantified based on a value of a magnitude of the motion sensor 470, determine a stable state of the user based on the variation in the heart rate of the user, the variation corresponding to a difference between the heart rate of the user and a resting heart rate of the user, determine whether the user performs a second exercise, based on the skin temperature trend, and determine the UI based on whether the user performs the first exercise, whether the user performs the second exercise, and the stable state of the user.

According to an embodiment of the disclosure, the processor 120, 440 may be configured to reduce the body temperature measurement period when the UI is similar to an index indicating an unstable state, and increase the body temperature measurement period when the UI is similar to an index indicating a stable state.

According to an embodiment of the disclosure, the wearable electronic device 101, 104, 200, 300, 400, 600 may further include a second thermistor 420, 625 configured to estimate the skin temperature trend of the user outside the wearable electronic device. The processor 120, 440 may be configured to correct a body temperature of the user acquired based on the body temperature measurement period using the temperature sensor 430, 500, 650, based on a measured value of the second thermistor 420, 625.

According to an embodiment of the disclosure, a method of operating a wearable electronic device 101, 104, 200, 300, 400, 600 may include operation 710 of determining whether the wearable electronic device 101, 104, 200, 300, 400, 600 is worn, operation 720 of determining whether an internal temperature by internal elements 602, 604, 605 of the wearable electronic device 101, 104, 200, 300, 400, 600 is within a reference temperature range that does not have an influence on a measurement of a body temperature of a user, based on whether the wearable electronic device 101, 104, 200, 300, 400, 600 is worn, operation 730 of determining a UI indicating whether the user is in a state in which the body temperature is measurable, when the internal temperature is determined to be within the reference temperature range, and operation 740 of measuring the body temperature by adjusting a body temperature measurement period based on the UI.

According to an embodiment of the disclosure, the wearable electronic device 101, 104, 200, 300, 400, 600 may include at least one first thermistor 410, 631, 633, 635 arranged in different heat generation positions in the wearable electronic device 101, 104, 200, 300, 400, 600 and configured to detect a temperature change of the internal elements 602, 604, 605. The determining of whether the internal temperature is within the reference temperature range may include determining whether the internal temperature by the internal elements 602, 604, 605 is within the reference temperature range, by a measured value of the at least one first thermistor 410, 631, 633, 635, based on whether the wearable electronic device 101, 104, 200, 300, 400, 600 is worn.

According to an embodiment of the disclosure, the internal elements 602, 604, 605 may include at least one of an AP 120, 605, a battery 189, 602, or a CP 120, 440.

According to an embodiment of the disclosure, the determining of whether the internal temperature is within the reference temperature range may include calculating a representative value of temperatures of the internal elements 602, 604, 605 based on the measured value of the at least one first thermistor 410, 631, 633, 635, and determining whether the representative value is within the reference temperature range.

According to an embodiment of the disclosure, the determining of whether the representative value is within the reference temperature range may include remeasuring a value of the at least one first thermistor 410, 631, 633, 635 after a reconfirmation time used for a temperature decrease for each of the temperatures of the internal elements 602, 604, 605 elapses, when the representative value is determined to be out of the reference temperature range, and determining whether the remeasured value of the first thermistor is within the reference temperature range.

According to an embodiment of the disclosure, the wearable electronic device 101, 104, 200, 300, 400, 600 may further include at least one of a second thermistor 420, 625 configured to estimate a skin temperature trend of the user outside the wearable electronic device 101, 104, 200, 300, 400, 600, a motion sensor 470 configured to detect a motion of the user, or a PPG sensor configured to detect a heart rate of the user. The determining of the UI may include estimating the skin temperature trend of the user wearing the wearable electronic device 101, 104, 200, 300, 400, 600 using a measured value of the second thermistor 420, 625, when the internal temperature is determined to be within the reference temperature range, and determining the UI based on at least one of the motion of the user, a variation in the heart rate of the user, or the skin temperature trend of the user.

According to an embodiment of the disclosure, the determining of the UI may include determining whether the user performs a first exercise, based on a degree of motion of the user quantified based on a value of a magnitude of the motion sensor 470, determining a stable state of the user based on the variation in the heart rate of the user, the variation corresponding to a difference between the heart rate of the user and a resting heart rate of the user, determining whether the user performs a second exercise based on the skin temperature trend, and determining the UI based on at least one of whether the user performs the first exercise, whether the user performs the second exercise, or the stable state of the user.

According to an embodiment of the disclosure, the measuring of the body temperature may include reducing the body temperature measurement period when the UI is similar to an index indicating an unstable state, and increasing the body temperature measurement period when the UI is similar to an index indicating a stable state.

According to an embodiment of the disclosure, the wearable electronic device 101, 104, 200, 300, 400, 600 may further include a second thermistor 420, 625 configured to estimate a skin temperature trend of the user outside the wearable electronic device 101, 104, 200, 300, 400, 600. The measuring of the body temperature may include acquiring the body temperature of the user based on the body temperature measurement period using the temperature sensor 430, 500, 650, and correcting the acquired body temperature based on a measured value of the second thermistor 420, 625.

What is claimed is:

1. A wearable electronic device comprising:

at least one first thermistor arranged in different heat generation positions in the wearable electronic device and configured to detect a temperature change of internal elements of the wearable electronic device;

a temperature sensor configured to calculate a body temperature of a user based on the temperature change of the internal elements and a skin temperature trend of the user; and at least one processor, comprising processing circuitry, individually and/or collectively configured to:

determine whether an internal temperature by the internal elements in the wearable electronic device is within a reference temperature range that does not have an influence on a calculation of the body temperature, based on a measured value of the at least one first thermistor, determine a user state index (UI) indicating whether the user is in a state in which the body temperature is measurable, when the internal temperature is determined to be within the reference temperature range, and measure the body temperature during a body temperature measurement period that is adjusted based on the UI, wherein the body temperature measurement period is increased based on decrease in the UI and the body temperature measurement period is decreased based on increase in the UI, wherein the UI is determined based on a combination of at least two of user state variables, including the skin temperature trend of user, a user motion, and a heart rate variation.

2. The wearable electronic device of claim 1, further comprising a contact sensor configured to detect whether the user is in contact with the wearable electronic device, wherein the at least one processor is further configured to determine whether the internal temperature is within the reference temperature range based on the measured value of the at least one first thermistor, when it is determined by the contact sensor that the user wears the wearable electronic device.

3. The wearable electronic device of claim 1, wherein the internal elements comprise at least one of an application processor (AP), a battery, or a communication processor (CP).

4. The wearable electronic device of claim 1, wherein the at least one processor is further configured to:

calculate a representative value of temperatures of the internal elements based on the measured value of the at least one first thermistor, and determine whether the representative value is within the reference temperature range.

5. The wearable electronic device of claim 4, wherein the at least one processor is further configured to assign different weights for each measured value of the at least one first thermistor and calculate the representative value.

6. The wearable electronic device of claim 4, wherein the at least one processor is further configured to:

remeasure a value of the at least one first thermistor after a reconfirmation time used for a temperature decrease for each of the temperatures of the internal elements elapses, when the representative value is determined to be out of the reference temperature range, and determine whether the remeasured value of the first thermistor is within the reference temperature range.

7. The wearable electronic device of claim 1, further comprising at least one of a motion sensor configured to detect a motion of the user, a photoplethysmogram (PPG) sensor configured to detect a heart rate of the user, or a second thermistor configured to estimate the skin temperature trend of the user outside the wearable electronic device, wherein the at least one processor is further configured to:

estimate the skin temperature trend of the user wearing the wearable electronic device using a measured value of the second thermistor, when the internal temperature is determined to be within the reference temperature range, and determine the UI based on the user state variables, including the skin temperature trend of user, a user motion, and a heart rate variation.

8. The wearable electronic device of claim 7, wherein the at least one processor is further configured to:

determine whether the user performs a first exercise, based on a degree of motion of the user quantified based on a value of a magnitude of the motion sensor, determine a stable state of the user based on the variation in the heart rate of the user, the variation corresponding to a difference between the heart rate of the user and a resting heart rate of the user, determine whether the user performs a second exercise, based on the skin temperature trend, and determine the UI based on whether the user performs the first exercise, whether the user performs the second exercise, and the stable state of the user.

9. The wearable electronic device of claim 1, wherein the at least one processor is further configured to:

reduce the body temperature measurement period when the UI is similar to an index indicating an unstable state, and increase the body temperature measurement period when the UI is similar to an index indicating a stable state.

10. The wearable electronic device of claim 1, further comprising a second thermistor configured to estimate the skin temperature trend of the user outside the wearable electronic device, wherein the at least one processor is configured to correct a body temperature of the user acquired based on the body temperature measurement period using the temperature sensor, based on a measured value of the second thermistor.

11. A method of operating a wearable electronic device, the method comprising:

determining whether the wearable electronic device is worn;

determining whether an internal temperature by internal elements of the wearable electronic device is within a reference temperature range that does not have an influence on a measurement of a body temperature of a user, based on whether the wearable electronic device is worn;

determining a user state index (UI) indicating whether the user is in a state in which the body temperature is measurable, when the internal temperature is determined to be within the reference temperature range; and measuring the body temperature during a body temperature measurement period that is adjusted based on the UI, wherein the body temperature measurement period is increased based on decrease in the UI and the body temperature measurement period is decreased based on increase in the UI, wherein the UI is determined based on a combination of at least two of user state variables, including a skin temperature trend, a user motion, and a heart rate variation.

12. The method of claim 11, wherein the wearable electronic device comprises at least one first thermistor arranged in different heat generation positions in the wearable electronic device and configured to detect a temperature change of the internal elements, and wherein the determining of whether the internal temperature is within the reference temperature range comprises determining whether the internal temperature by the internal elements is within the reference temperature range, by a measured value of the at least one first thermistor, based on whether the wearable electronic device is worn.

13. The method of claim 12, wherein the internal elements comprise at least one of an application processor (AP), a battery, or a communication processor (CP).

14. The method of claim 13, wherein the determining of whether the internal temperature is within the reference temperature range comprises:

calculating a representative value of temperatures of the internal elements based on the measured value of the at least one first thermistor; and determining whether the representative value is within the reference temperature range.

15. The method of claim 14, wherein the determining of whether the representative value is within the reference temperature range comprises:

remeasuring a value of the at least one first thermistor after a reconfirmation time used for a temperature decrease for each of the temperatures of the internal elements elapses, when the representative value is determined to be out of the reference temperature range; and determining whether the remeasured value is within the reference temperature range.

16. The method of claim 11, wherein the wearable electronic device further comprises at least one of a second thermistor configured to estimate a skin temperature trend of the user outside the wearable electronic device, a motion sensor configured to detect a motion of the user, or a photoplethysmogram (PPG) sensor configured to detect a heart rate of the user, and wherein the determining of the UI comprises:

estimating the skin temperature trend of the user wearing the wearable electronic device using a measured value of the second thermistor, when the internal temperature is determined to be within the reference temperature range, and determining the UI based on the user state variables, including the skin temperature trend of user, a user motion, and a heart rate variation.

17. The method of claim 16, wherein the determining of the UI comprises:

determining whether the user performs a first exercise, based on a degree of motion of the user quantified based on a value of a magnitude of the motion sensor;

determining a stable state of the user based on the variation in the heart rate of the user, the variation corresponding to a difference between the heart rate of the user and a resting heart rate of the user;

determining whether the user performs a second exercise based on the skin temperature trend; and determining the UI based on at least one of whether the user performs the first exercise, whether the user performs the second exercise, or the stable state of the user.

18. The method of claim 11, wherein the measuring of the body temperature comprises:

reducing the body temperature measurement period when the UI is similar to an index indicating an unstable state; and increasing the body temperature measurement period when the UI is similar to an index indicating a stable state.

19. The method of claim 11, wherein the wearable electronic device further comprises a second thermistor configured to estimate a skin temperature trend of the user outside the wearable electronic device, and wherein the measuring of the body temperature comprises:

acquiring the body temperature of the user based on the body temperature measurement period using a temperature sensor, and correcting the acquired body temperature based on a measured value of the second thermistor.

20. The method of claim 15, further comprising:

assigning different weights for each measured value of the at least one first thermistor and calculating the representative value.

* * * * *